US007148253B2

(12) United States Patent
Wu et al.

(10) Patent No.: US 7,148,253 B2
(45) Date of Patent: Dec. 12, 2006

(54) 4-THIO COUMARINS

(75) Inventors: Jie Wu, Ridgewood, NJ (US); Zhen Yang, Ridgewood, NJ (US); Reza Fathi, Hohokus, NJ (US); Qiang Zhu, Ridgewood, NJ (US)

(73) Assignee: XTL Biopharmaceuticals Ltd., Rehovet (IL)

( * ) Notice: Subject to any disclaimer, the term of this patent is extended or adjusted under 35 U.S.C. 154(b) by 0 days.

(21) Appl. No.: 10/752,654

(22) Filed: Jan. 6, 2004

(65) Prior Publication Data
US 2004/0180950 A1 Sep. 16, 2004

Related U.S. Application Data

(63) Continuation-in-part of application No. 10/437,768, filed on May 13, 2003, now Pat. No. 6,703,514.

(60) Provisional application No. 60/380,487, filed on May 14, 2002.

(51) Int. Cl.
*A61K 31/35* (2006.01)

(52) U.S. Cl. .................. 514/456; 514/457; 549/284; 549/285

(58) Field of Classification Search ............. 549/285, 549/284; 514/456, 457
See application file for complete search history.

(56) References Cited

U.S. PATENT DOCUMENTS

| | | | |
|---|---|---|---|
| 5,681,968 A | 10/1997 | Alvarado et al. | |
| 5,759,959 A | 6/1998 | Alvarado et al. | |
| 5,808,105 A | 9/1998 | Alvarado et al. | |
| 6,034,121 A | 3/2000 | O'Mahony et al. | |
| 6,703,514 B1 * | 3/2004 | Wu et al. | 549/284 |

OTHER PUBLICATIONS

Siddiq, M et al 'Reactions of 4, or 3,4-disubstituted coumarins with nucleophilic reagents' J. Chem Soc. 5(2) (19983) pp. 73-77.*
Martin Kovic, "Synthesis of Coumarin Sulfonamides and Sulfonylurea," Arkivoc, 2001, part (iv), pp. 100-108.
Parfenov et al., Khim. Gererotsikl. Soedin., 1991, 8, 1032-1037.
Wu, J. et al., "Synthesis of 4-Substituted Coumarins via the Palladium-Catalyzed Cross-Couplings of 4-Tosylcoumarins with Terminal Acetylenes and Organozinc Reagents," J. Org. Chem. 2001, 66, 3642-3645.
Laurin, P. et al., "Synthesis and In Vitro Evaluation of Novel Highly Potent Coumarin Inhibitors of Gyrase B," Bioorg. Med. Chem. Letters 9, 1999, pp. 2079-2084.
Appendino, G. et al., "A Straightforward Entry into Polyketide Monoprenylated Furanocoumarins," J. Nat. Prod. 1999, 62, pp. 1627-1631.
Guillier et al., "Linkers and Cleavage Strategies in Solid-Phase Organic Synthesis and Combinatorial Chemistry" Chem. Rev. 2000, 100, 2091-2157.
Sternson et al., "Split-Pool Synthesis of 1, 3-Dioxanes Leading to Arrayed Stock Solutions of Single Compounds Sufficient for Multiple Phenotypic and Protein-Binding Assays," J. Am. Chem. Soc. 2001, 123, pp. 1740-1741.
Blackwell et al., Exploiting Site-Site Interactions on Solid Support to Generate Dimeric Molecules, Organic Letters, 2001, vol. 3, No. 8, pp. 1185-1188.
Pelish et al. "Use of Biomimetic Diversity-Oriented Synthesis to Discover Galanthamine-Like Molecules with Biological Properties Beyond Those of the Natural Product," J. Am. Chem. Soc. 2001, 123, 6740-6741.
Tallarico et al., "An Alkylsilyl-Tethered, High-Capacity Solid Support Amenable to Diversity-Oriented Synthesis for One-Bead, One-Stock Solution Chemical Genetics," J. Comb. Chem. 2001, 3, pp. 312-318.
Greene, T. W. et al., "Protective Groups in Organic Synthesis," 2nd ed., Wiley: New York, 1991.
Remington's Pharmaceutical Sciences, "The Science and Practice of Pharmacy," 19. Ed. Mack Publishing Company, Easton, PA., 1995.
Ross et al., "Quantitation of Hepatitis C Virus RNA by Third Generation Branched Dna-based Signal Amplification Assay," J. Virological Methods, 2002, 101, pp. 159-168.
Korba, B. E. et al., "Use of a Standardized Cell Culture Assay to Assess Activities of Nucleoside Analogs Against Hepatitis B Virus Replication," Antiviral Research, 1992, 19, pp. 55-70.
Blight et al., "Efficient Initiation of HCV RNA Replication in Cell Culture," Science, Dec. 8, 2000, vol. 290, pp. 1972-1974.
Majundar, K.C. et al., "Studies of bioactive heterocycles: facile thio-Claisen rearrangement of propagylthio[1]benzopyran-2-ones" Tetrahedron Letters 43 (2002) 2115-2117.
Supplementary European Search Report, issued Jun. 8, 2006.

* cited by examiner

*Primary Examiner*—Amelia A. Owens
(74) *Attorney, Agent, or Firm*—Kenyon & Kenyon LLP

(57) ABSTRACT

4-Thio substituted coumarin derivatives, 4,5-dithio substituted coumarin derivatives, and coumarin dimers are provided, as well as processes for their preparation. The invention also provides a method and composition for the treatment of hepatitis C virus (HCV) by adiministering 4-thio substituted coumarin derivatives, 4,5-dithio substituted coumarin derivatives, and coumarin dimers.

31 Claims, No Drawings

4-THIO COUMARINS

RELATED APPLICATIONS

This application is a continuation-in-part of U.S. application Ser. No. 10/437,768, filed May 13, 2003 now U.S. Pat. No. 6,703,514, and claims the benefit of U.S. Provisional Application No. 60/380,487, filed May 14, 2002, each of which are incorporated herein by reference in their entireties.

FIELD OF THE INVENTION

The present invention relates to novel 4-thio substituted coumarin derivatives and coumarin dimers, and processes for their preparation. The invention provides a synthetic process for the preparation of 4-thio substituted coumarin derivatives using mild reaction conditions, which provides a high substituent tolerance and is appropriate for use in solid phase syntheses for producing a library of 4-thio substituted coumarin derivatives for biological screening.

BACKGROUND OF THE INVENTION

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity. Of particular interest are materials which have structural components, such as coumarins, flavones, and isoflavones, which are similar to secondary metabolites from plant extracts.

Coumarins are widely distributed in the plant kingdom. Approximately 50 naturally occurring coumarin derivatives have been identified. Derivatives of coumarin posses a range of biological activities. Of particular interest to researchers are modification at the 3- and 4-position of the coumarin scaffold and synthesis of symmetrical and unsymmetric dimers of coumarin compounds for biological evaluations. To avoid confusion, the coumarin derivatives described herein are numbered according to the following convention:

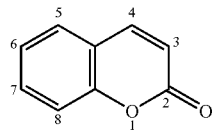

Unfortunately, the preparation of such coumarin derivatives has suffered from multiple difficulties. This is particularly true of 4-substituted thiol derivatives of coumarin. Although certain 4-thio coumarins have been prepared, their synthesis has involved harsh conditions (such as the use of stoichiometric amounts of strong bases or toxic reagents, often under high temperatures, multiple synthetic steps, and poor substituent tolerance. For example, Parfenov et al. discussed a route for synthesis of 4-coumarinyl sulfides derivatives from 4-tosyl coumarin using harsh reaction conditions or from 4-chloro coumarin, which was generated under acidic conditions and high temperature. Parfenov et al., *Khim. Gererotsikl. Soedin.*, 1991, 8, 1032. It is known that the selectivity of the reaction of 4-hydroxycoumarin with chlorinating reagents such as $PCl_5$ and $POCl_3$ is low, because a considerable amount of 4-chloro-3,4,3',4''-tercoumarin will be formed as a by-product. Also reported with regard to substituted 4-thio coumarin derivatives, is a paper by Martin Kovič, in ARKIVOC, 2001, part (vi), which utilizes 4-chlorocoumarin as an intermediate to synthesize 4-ethylthiocoumarin under basic conditions at elevated temperature (reflux) using sodium ethanethiol. Although a high yield of product was obtained by this methodology, it is not applicable to the production of a large variety of 4-thiol substituted derivatives with a diverse substitution pattern because of the harsh reaction conditions (both acidic and basic) used to arrive at the product. Extension of this route to solid supported synthesis for production of a combinatorial library is limited due to the acid sensitivity of many common solid support linkers.

Infection with the Hepatitis C virus (HCV) represents a serious world-wide health crisis. In more than 70% of infected individuals, the virus evades clearance by the immune system leading to a persistent HCV infection. The long term effects of persistent HCV infection range from an apparently healthy carrier state to chronic hepatitis, liver fibrosis, cirrhosis, and eventually hepatocellular carcinoma. HCV is a leading cause of chronic liver disease. The best therapy currently available for treatment of HCV infection uses a combination of pegylated α-interferon and ribavirin. However, many of the patients treated with this therapy fail to show a sufficient antiviral response. Additionally, interferon treatment also induces severe side-effects (i.e. retinopathy, thyroiditis, acute pancreatitis, depression) that diminish the quality of life of treated patients. Thus, it is vital that more effective treatments be identified.

SUMMARY OF THE INVENTION

The present invention is directed to certain 4-thio substituted coumarin derivatives of the formula I

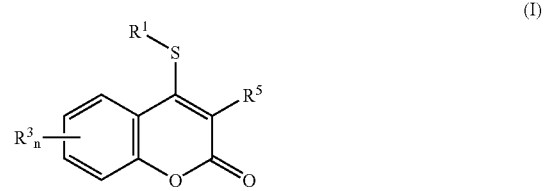

wherein
$R^1$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

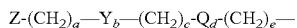

wherein Y and Q are independently selected from an aromatic group, O, S, —CR=CR—,

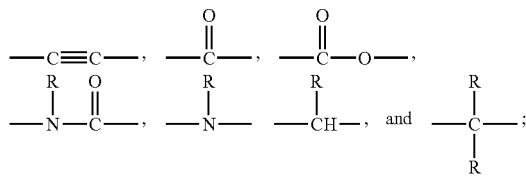

each R is independently selected from H or lower alkyl, Z is selected from H, —CO$_2$R, —OR, —SR, —NR$_2$,

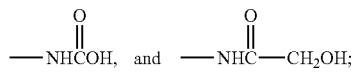

a, c and e are independently selected from values from 0 to 10;

b and d are independently selected from 0 and 1, provided that when a=0 then b=0, and when c=0 then d=0;

or $R^3$ may occupy two adjacent positions to form a fused aromatic ring, n is selected from values between 0 and 4;

$R^5$ is selected from hydrogen, lower alkyl, lower alkenyl, lower alkynyl, lower aralkyl, aryl, thioalkyl, thioaryl, and thioaralkyl, each of which may be unsubstituted or substituted with one or more substituents selected from halogen, lower alkyl, and lower alkoxy, thio-lower alkyl, $C_1$–$C_8$ acyl, lower alkyl ester, amide, and lower alkyl amide; or $R^5$ may be a group of the formula

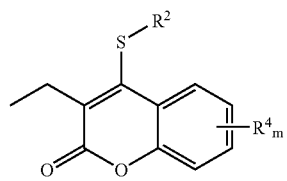

wherein
$R^2$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

$R^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^4$ is a group of the formula

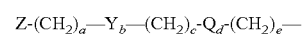

wherein Y and Q are independently selected from an aromatic group, O, S, —CR=CR—,

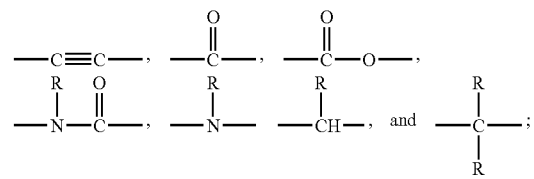

each R is independently selected from H or lower alkyl, Z is selected from H, —CO$_2$R, —OR, —SR, —NR$_2$,

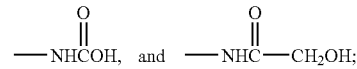

a, c and e are independently selected from values from 0 to 10;

b and d are independently selected from 0 and 1, provided that when a=0 then b=0, and when c=0 then d=0;

or $R^4$ may occupy two adjacent positions to form a fused aromatic ring, and, m is selected from values between 0 and 4.

Therefore, the present invention provides for symmetrical and unsymmetrical dimeric forms of 4-thio-substituted coumarin derivatives of the formula II:

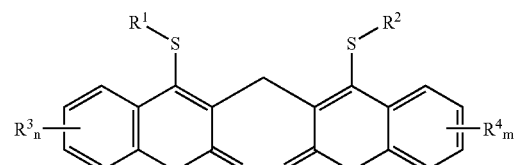

wherein
$R^1$ and $R^2$ are independently selected from an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

each $R^3$ and $R^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula

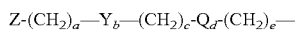

wherein Y and Q are independently selected from an aromatic group, O, S, —CR═CR—,

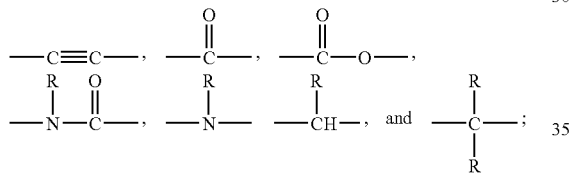

each R is independently selected from H or lower alkyl, Z is selected from H, —$CO_2R$, —OR, —SR, —$NR_2$,

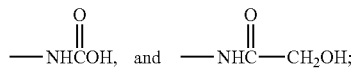

a, c and e are independently selected from values from 0 to 10;

b and d are independently selected from 0 and 1, provided that when a=0 then b=0, and when c=0 then d=0;

or $R^3$ or $R^4$ may occupy two adjacent positions to form a fused aromatic ring, n and m are independently selected from values between 0 and 4.

The invention also provides for 4-thio coumarin derivatives of the formula III:

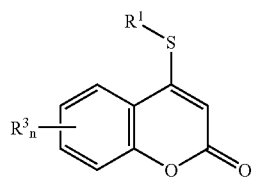

wherein $R^1$ and $R^3$ and n are as described above for compound I.

The invention further provides for 4-thio coumarin derivatives of the formula X

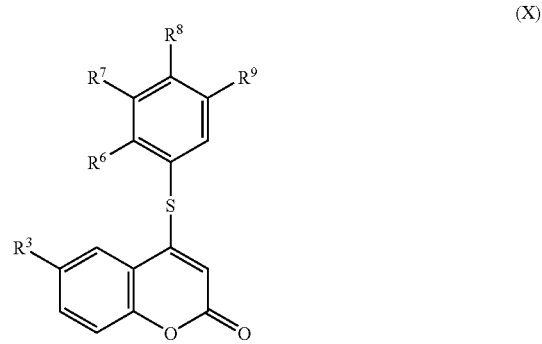

wherein $R^3$ is as described for the compound of formula I, $R^6$ is selected from halogen, halogenated methyl, methoxy, and ethoxy;

$R^7$ is selected from H, halogen, halogenated methyl, methoxy, and ethoxy;

$R^8$ is selected from H, halogen, halogenated methyl, methoxy, and ethoxy, and $R^9$ is selected from H, halogen, halogenated methyl, methoxy, and ethoxy.

The invention further provides compounds of the formula XI:

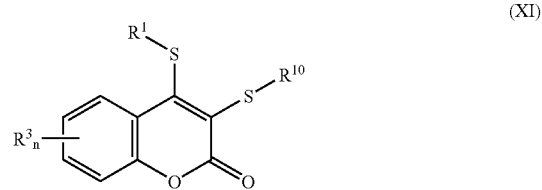

wherein $R^1$ and $R^{10}$ are independently selected from an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

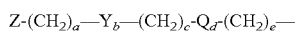

wherein Y and Q are independently selected from an aromatic group, O, S, —CR=CR—,

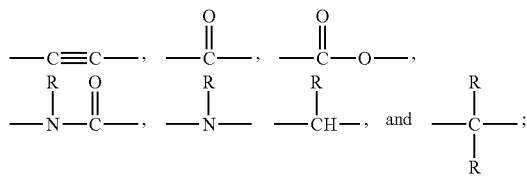

each R is independently selected from H or lower alkyl, Z is selected from H, —$CO_2R$, —OR, —SR, —$NR_2$,

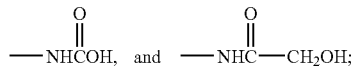

a, c and e are independently selected from values from 0 to 10;

b and d are independently selected from 0 and 1, provided that when a=0 then b=0, and when c=0 then d=0;

or $R^3$ may occupy two adjacent positions to form a fused aromatic ring; and n is selected from values between 0 and 4.

The invention also provides a synthetic process for the preparation of compounds of the formula I. The process uses mild reaction conditions, which provides a high substituent tolerance. Thus, the process is applicable to the preparation of a wide variety of 4-thio substituted coumarin derivatives with diverse substitution patterns. Additionally, the process is appropriate for use with the solid-support (solid phase) synthesis of 4-thio substituted coumarin derivatives. Thus, the process provides a method for producing a library of 4-thio substituted coumarin derivatives for biological screening.

The invention also provides compositions and methods for the treatment of HCV by administering a compound of the present invention in a therapeutically effective amount.

DETAILED DESCRIPTION OF THE PREFERRED EMBODIMENTS

The term "halo" or "halogen" as used herein includes fluorine, chlorine, bromine and iodine.

The term "alkyl" as used herein contemplates both straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl, and the like.

The term "cycloalkyl" as used herein contemplates cyclic alkyl radicals containing form 3 to 7 carbon atoms and includes cyclopropyl, cyclopentyl, cyclohexyl, and the like.

The term "lower alkenyl" as used herein contemplates both straight and branched chain alkene radicals containing from two to six carbon atoms.

The term "lower alkynyl" as used herein contemplates both straight and branched chain alkyne radicals containing from two to six carbon atoms.

The term "thioalkyl" as used herein refers to a group having the formula —S-lower alkyl.

The term "thioaryl" as used herein refers to a group having the formula —S-aryl. In preferred embodiments, the aryl portion is a phenyl group.

The term "$C_2$–$C_8$ acyl" as used herein contemplates both straight and branched chain acyl radicals containing from two to eight carbon atoms and includes acetyl, propionyl, 2-methylbutyryl and the like.

The term "lower alkyl ester" as used herein contemplates the straight and branched chain lower alkyl esters including —$CO_2CH_3$, —$CO_2CH_2CH_3$, —$CO_2CH(CH_3)CH_2CH_3$, and the like.

The term "lower alkyl amide" as used herein contemplates the straight and branched chain lower alkyl amides including

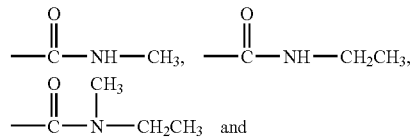

the like.

The terms "aralkyl" as used herein contemplates a lower alkyl group which has as a substituent an aromatic group.

The term "aromatic group" as used herein contemplates 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aromatic groups having heteroatoms in the ring structure may also be referred to as "aryl heterocycles" or "heteroaromatics". The term aromatic groups also includes polycyclic ring systems having two or more rings in which two carbons are common to two adjoining rings (the rings are "fused") wherein at least one of the rings is aromatic, e.g., the other rings can be cycloalkyls, cycloalkenyls, aryl, heterocycles and/or heteroaryls.

All value ranges, for example those given for n and m, are inclusive over the entire range. Thus, a range between 0–4 would include the values 0, 1, 2, 3 and 4.

One embodiment of the present invention pertains to novel 4-thio-coumarin derivatives of the formula I:

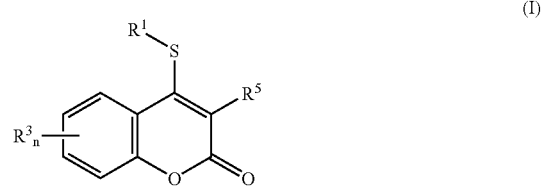

wherein $R^1$ is selected from an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

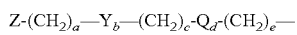

wherein Y and Q are independently selected from an aromatic group, O, S, —CR═CR—,

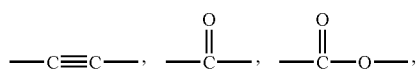

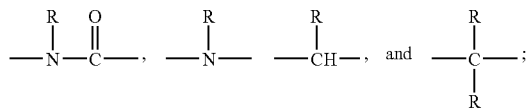

each R is independently selected from H or lower alkyl, Z is selected from H, —$CO_2R$, —OR, —SR, —$NR_2$,

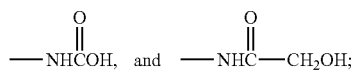

a, c and e are independently selected from values from 0 to 10;

b and d are independently selected from 0 and 1, provided that when a=0 then b=0, and when c=0 then d=0;

or $R^3$ may occupy two adjacent positions to form a fused aromatic ring, n is selected from values between 0 and 4;

$R^5$ is selected from hydrogen, lower alkyl, lower alkenyl, lower alkynyl, lower aralkyl, aryl, thioalkyl, thioaryl, and thioaralkyl, each of which may be unsubstituted or substituted with one or more substituents selected from halogen, lower alkyl, and lower alkoxy, thio-lower alkyl, $C_1$–$C_8$ acyl, lower alkyl ester, amide, and lower alkyl amide; or $R^5$ may be a group of the formula

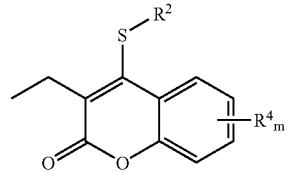

wherein
$R^2$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

$R^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^4$ is a group of the formula

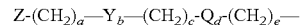

wherein Y and Q are independently selected from an aromatic group, O, S, —CR═CR—,

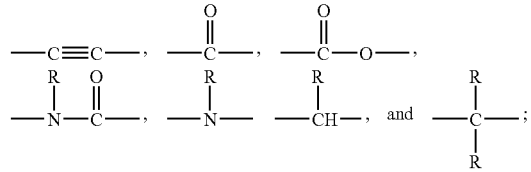

each R is independently selected from H or lower alkyl, Z is selected from H, —$CO_2R$, —OR, —SR, —$NR_2$,

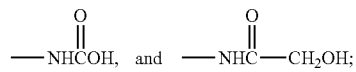

a, c and e are independently selected from values from 0 to 10;

b and d are independently selected from 0 and 1, provided that when a=0 then b=0, and when c=0 then d=0;

or $R^4$ may occupy two adjacent positions to form a fused aromatic ring, and, m is selected from values between 0 and 4.

It is understood that when n is a value greater than 1, each $R^3$ group may be selected independently. Thus, when more than one $R^3$ group is present, the $R^3$ groups may be selected from any of the stated groups so as to be the same or different. This also holds true for $R^4$ when m has a value of greater than 1, and for any other group or substituent which may be selected independently from among various groups or values.

When Y or Q is an ester or amide functionality,

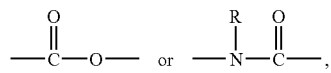

the group may be in either available orientation. Thus, for example, when Y is

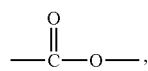

then $R^3$ may be chosen from

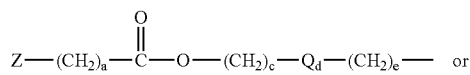

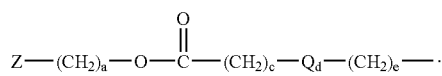

When one or more chiral centers are present in the compounds of the present invention, the individual isomers and mixtures thereof (e.g., racemates, etc.) are intended to be encompassed by the formulae depicted herein.

In one embodiment of the invention, the 3-position of the 4-thio substituted coumarin is unsubstituted ($R^5$ is H) giving a compound of the formula III:

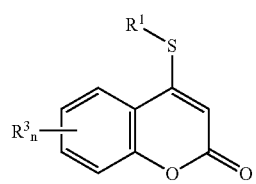

wherein $R^1$, $R^3$ and n are as described above. In a preferred embodiment, $R^1$ is phenyl or substituted phenyl. Table 1 provides representative compounds of the formula III.

TABLE 1

| Comp. No. | $R^1$ | $R^3$ | purity (%) |
|---|---|---|---|
| 9h-B1 | phenyl | 7-OH | 94.7 |
| 9h-B2 | 2-bromophenyl | 7-OH | 94.6 |
| 9h-B3 | 3-bromophenyl | 7-OH | 91.8 |
| 9h-B4 | 4-bromophenyl | 7-OH | >99 |
| 9h-B19 | 3,4-dimethylphenyl | 7-OH | 77.8 |
| 9h-B18 | 2,4-dimethylphenyl | 7-OH | 85.9 |
| 9h-B21 | 2,6-dimethylphenyl | 7-OH | 87.0 |
| 9h-B30 | 3,5-dimethylphenyl | 7-OH | 83.5 |
| 9h-B24 | 2,4-dimethylphenyl | 7-OH | 94.5 |
| 9h-B15 | 2-ethylphenyl | 7-OH | 95.4 |

TABLE 1-continued

| Comp. No. | R¹ | R³ | purity (%) |
|---|---|---|---|
| 9h-B5 | 2-methylphenyl (o-CH₃) | 7-OH | 89.2 |
| 9h-B6 | 3,5-dimethylphenyl | 7-OH | 83.6 |
| 9h-B8 | 4-methylphenyl (p-CH₃) | 7-OH | 90.9 |
| 9h-B7 | 2-chlorophenyl | 7-OH | 96.5 |
| 9h-B9 | 3-chlorophenyl | 7-OH | 93.1 |
| 9h-B10 | 4-chlorophenyl | 7-OH | 97.7 |
| 9h-B11 | 2-methoxyphenyl | 7-OH | >99 |
| 9h-B12 | 3-methoxyphenyl | 7-OH | >99 |
| 9h-B13 | 2,4-difluorophenyl | 7-OH | >99 |
| 9h-B14 | 4-methoxyphenyl | 7-OH | 94.3 |
| 9h-B22 | 2-tert-butylphenyl | 7-OH | 88.0 |
| 9h-B27 | 2-naphthyl | 7-OH | 98.2 |
| 9h-B29 | 2,5-dimethoxy-4-methylphenyl | 7-OH | 95.3 |
| 9h-B23 | 2,4-dichlorophenyl | 7-OH | 94.2 |
| 9h-B26 | 3,4-dichlorophenyl | 7-OH | 93.8 |
| 9h-B17 | 4-fluorophenyl | 7-OH | >99 |
| 9h-B31 | 4-tert-butylphenyl | 7-OH | 74.9 |
| 9h-B16 | 3-fluorophenyl | 7-OH | >99 |
| 9h-B20 | 2-fluorophenyl | 7-OH | 97.9 |
| 9h-B28 | 4-(methylthio)phenyl | 7-OH | 94.1 |
| 9h-B25 | 2,6-dichlorophenyl | 7-OH | 97.7 |

TABLE 1-continued
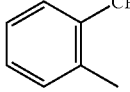
| Comp. No. | R¹ | R³ | purity (%) |
|---|---|---|---|
| 3a-B5 | 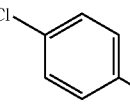 | — | 100 |
| 3a-B10 | 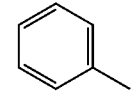 | — | 100 |
| 3b-B1 | 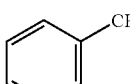 | 6-CH₃ | 100 |
| 3b-B5 | 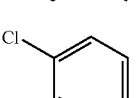 | 6-CH₃ | 100 |
| 3b-B10 | 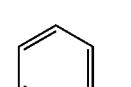 | 6-CH₃ | 100 |
| 3c-B1 | 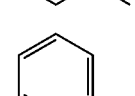 | 6-Cl | 100 |
| 3d-B1 | 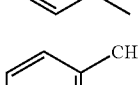 | 7-OCH₃ | 100 |
| 3d-B5 | 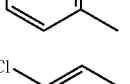 | 7-OCH₃ | 100 |
| 3d-B10 | 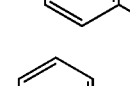 | 7-OCH₃ | 100 |
| 9i-B1 | 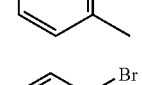 | 7-OH, 8-CH₃ | >99 |
| 9i-B2 | 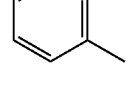 | 7-OH, 8-CH₃ | 98.9 |
| 9i-B3 | 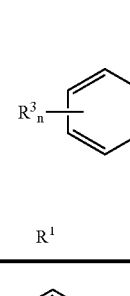 | 7-OH, 8-CH₃ | >99 |
TABLE 1-continued
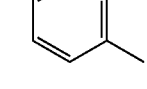
| Comp. No. | R¹ | R³ | purity (%) |
|---|---|---|---|
| 9i-B4 | 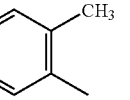 | 7-OH, 8-CH₃ | >99 |
| 9i-B5 | 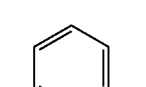 | 7-OH, 8-CH₃ | 96.9 |
| 9i-B6 | 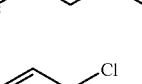 | 7-OH, 8-CH₃ | 97.6 |
| 9i-B7 | 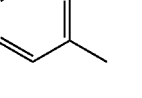 | 7-OH, 8-CH₃ | >99 |
| 9i-B31 | 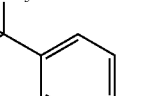 | 7-OH, 8-CH₃ | 84.5 |
| 9i-B20 | 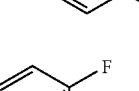 | 7-OH, 8-CH₃ | 95.5 |
| 9i-B16 | 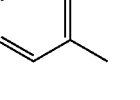 | 7-OH, 8-CH₃ | 96.4 |
| 9i-B28 | 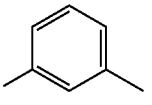 | 7-OH, 8-CH₃ | >99 |
| 9i-B13 | 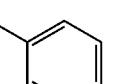 | 7-OH, 8-CH₃ | 94.8 |
| 9i-B29 | 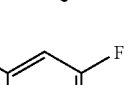 | 7-OH, 8-CH₃ | 97.7 |

TABLE 1-continued

| Comp. No. | R¹ | R³ | purity (%) |
|---|---|---|---|
| 9i-B22 | 2-tert-butylphenyl (CH₃,CH₃,CH₃) | 7-OH, 8-CH₃ | 72.9 |
| 9i-B27 | 2-naphthyl | 7-OH, 8-CH₃ | >99 |
| 9j-B1 | phenyl | 6-OH | 98.4 |
| 9j-B13 | 2,4-difluorophenyl | 6-OH | >99 |
| 9j-B29 | 2,4-dimethoxyphenyl | 6-OH | >99 |
| 9j-B22 | 2-tert-butylphenyl | 6-OH | 93.6 |
| 904 | 2-fluorophenyl | 6-F | >99 |
| 902 | 2,6-dichlorophenyl | 6-F | >99 |
| 901 | 2,4-dichlorophenyl | 6-F | >99 |
| 910 | 2,4-difluorophenyl | 6-F | >99 |
| 894 | 2-chlorophenyl | 6-F | >99 |
| 899 | 2-chloro-4-fluorophenyl | 6-F | >99 |
| 877 | 2-chlorophenyl | 5,6-fused benzene | >99 |
| 824 | 2-fluorophenyl | 6-OCH₃ | >99 |
| 830 | 2,4-difluorophenyl | 6-OCH₃ | >99 |

In a further embodiment of the invention, the 4-thio substituted coumarin is a compound of the formula X

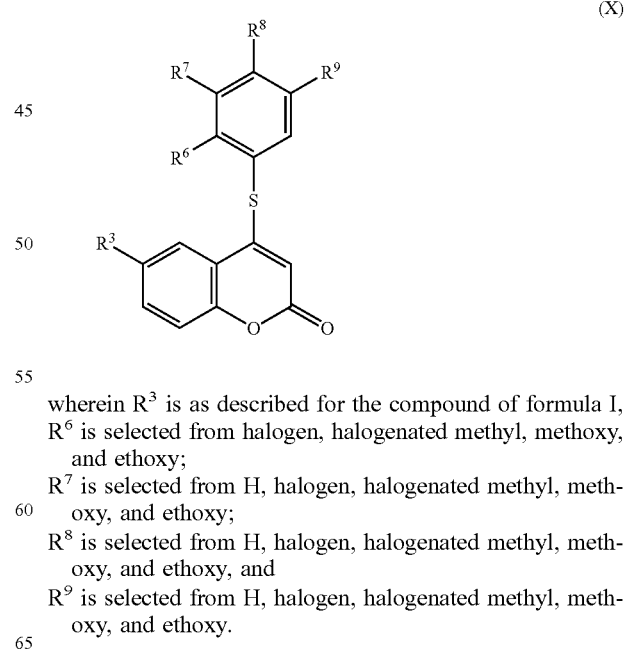

wherein $R^3$ is as described for the compound of formula I,
$R^6$ is selected from halogen, halogenated methyl, methoxy, and ethoxy;
$R^7$ is selected from H, halogen, halogenated methyl, methoxy, and ethoxy;
$R^8$ is selected from H, halogen, halogenated methyl, methoxy, and ethoxy, and
$R^9$ is selected from H, halogen, halogenated methyl, methoxy, and ethoxy.

In a preferred embodiment for compounds of the formula X, $R^7$ is hydrogen and $R^3$ is selected from halogen and lower alkoxy. In a further preferred embodiment, when $R^3$, $R^6$, $R^7$, or $R^8$ is a halogen, the halogen is preferably fluorine or chlorine.

The invention further provides compounds of the formula XI:

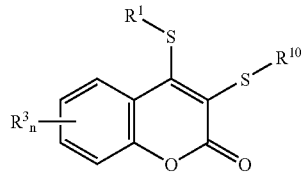
(XI)

wherein
$R^1$ and $R^{10}$ are independently selected from
  an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  an unsubstituted or substituted alkyl group, wherein the substituted alkyl group may be substituted with one or more halogen, hydroxy, and lower alkoxy; and
  an unsubstituted or substituted cycloalkyl group, wherein the substituted cycloalkyl group may be substituted with one or more halogen, hydroxy, and lower alkoxy;
$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

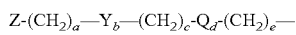

wherein Y and Q are independently selected from an aromatic group, O, S, —CR═CR—,

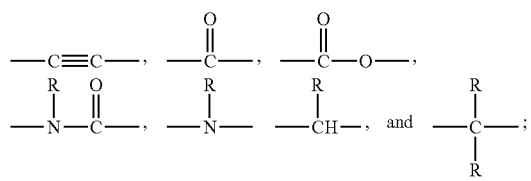

each R is independently selected from H or lower alkyl,
Z is selected from H, —$CO_2R$, —OR, —SR, —$NR_2$,

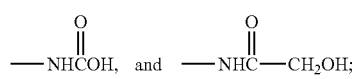

a, c and e are independently selected from values from 0 to 10;
b and d are independently selected from 0 and 1, provided that when a=0 then b=0, and when c=0 then d=0;
or $R^3$ may occupy two adjacent positions to form a fused aromatic ring; and
n is selected from values between 0 and 4.

In a preferred embodiment of the invention, $R^1$ and $R^{10}$ of a compound of the formula XI are selected from phenyl or substituted phenyl to give a compound of the formula XII

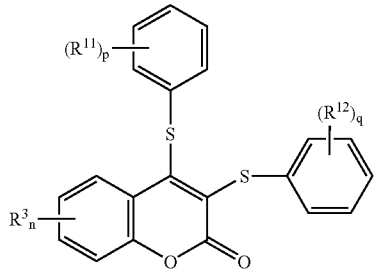
(XII)

wherein
  each $R^{11}$ is independently selected from halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  each $R^{12}$ is independently selected from halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  $R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

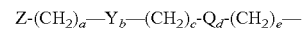

wherein Y and Q are independently selected from an aromatic group, O, S, —CR═CR—,

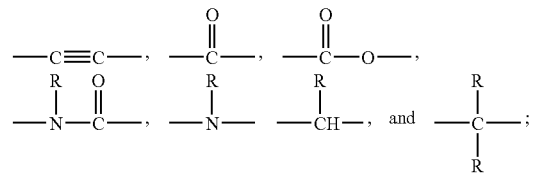

each R is independently selected from H or lower alkyl,
Z is selected from H, —$CO_2R$, —OR, —SR, —$NR_2$,

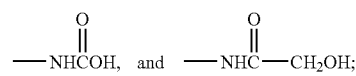

a, c and e are independently selected from values from 0 to 10;
b and d are independently selected from 0 and 1, provided that when a=0 then b=0, and when c=0 then d=0;
or $R^3$ may occupy two adjacent positions to form a fused aromatic ring;
n is selected from values between 0 and 4;

p is selected from values between 0 and 5; and q is selected from values between 0 and 5.

In a further preferred embodiment, n is 0 for the compound of formula XII, giving a compound of the formula XII$_a$

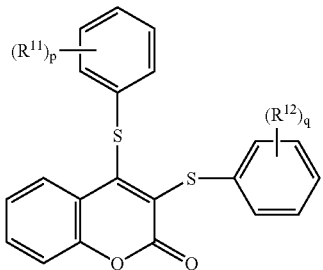

(XII$_a$)

wherein R$^{11}$, R$^{12}$, p and q are as described for the compound of formula XII. Table 2 provides compounds of the formula XII$_a$.

TABLE 2

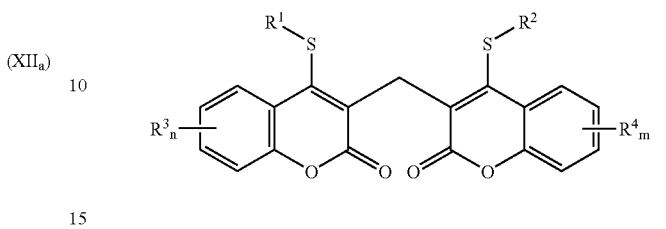

| Comp. No. | R$^{11}$ | R$^{12}$ |
|---|---|---|
| 412 | 4-Br | 4-F |
| 437 | 2-Cl, 4-F | 3-CH$_3$, 4-CH$_3$ |
| 468 | 3-Cl | 3-CH$_3$, 5-CH$_3$ |
| 473 | 2-Cl, 4-F | 3-CH$_3$, 5-CH$_3$ |

In another embodiment of the present invention, the 3-position of the 4-thio substituted coumarin is substituted with a group of the formula:

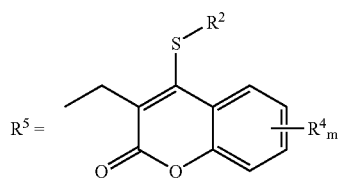

resulting in a symmetric or unsymmetric coumarin dimer having the formula (II):

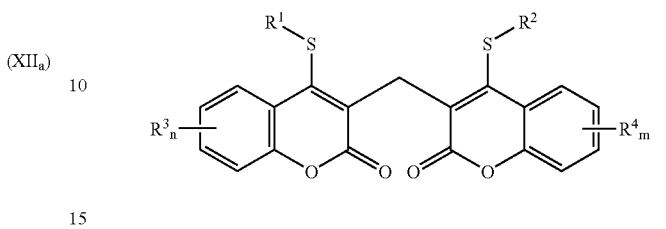

(II)

wherein

R$^1$ and R$^2$ are independently selected from an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, C$_1$–C$_8$ acyl, lower alkyl ester, amide, and lower alkyl amide;

a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, C$_1$–C$_8$ acyl, lower alkyl ester, amide, and lower alkyl amide;

an unsubstituted or substituted alkyl group, wherein the substituted alkyl group may be substituted with one or more halogen, hydroxy, and lower alkoxy; and an unsubstituted or substituted cycloalkyl group, wherein the substituted cycloalkyl group may be substituted with one or more halogen, hydroxy, and lower alkoxy;

each R$^3$ and R$^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula Z-(CH$_2$)$_a$—Y$_b$—(CH$_2$)$_c$-Q$_d$-(CH$_2$)$_e$— wherein Y and Q are independently selected from an aromatic group, O, S, —CR=CR—,

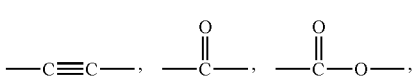

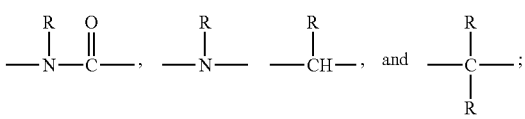

each R is independently selected from H or lower alkyl,

Z is selected from H, —CO$_2$R, —OR, —SR, —NR$_2$,

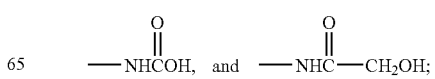

a, c and e are independently selected from values from 0 to 10;

b and d are independently selected from 0 and 1, provided that when a=0 then b=0, and when c=0 then d=0;

or $R^3$ or $R^4$ may occupy two adjacent positions to form a fused aromatic ring, n and m are independently selected from values between 0 and 4.

In one embodiment of the invention, the 5-, 6-, 7-, and 8-positions of the 4-thio substituted coumarin dimers are unsubstituted (n and m are 0) giving a compound of the formula $II_a$:

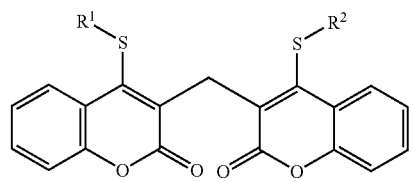

(II$_a$)

wherein $R^1$, $R^3$ and are as described above with respect to formula II. Table 3 provides representative compounds of the formula $II_a$.

TABLE 3

| Comp. No. | $R^1$ | $R^2$ | purity |
|---|---|---|---|
| 94-B1 | phenyl | phenyl | 100% |
| 56-C3 | 3,4-dimethylphenyl | 3,4-dimethylphenyl | >99% |
| 56-C3 | 4-methylphenyl | 4-methylphenyl | 100% |
| 56-C4 | 4-chlorophenyl | 4-chlorophenyl | 100% |
| 56-C5 | 4-fluoro-2-chlorophenyl | 4-fluoro-2-chlorophenyl | 100% |
| 56-C6 | 2-naphthyl | 2-naphthyl | 100% |
| 56-C7A | 2,5-dichlorophenyl | 2,5-dichlorophenyl | 100% |
| 56-C9 | 3,4-dichlorophenyl | 3,4-dichlorophenyl | 100% |

TABLE 3-continued
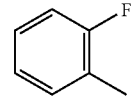
| Comp. No. | R¹ | R² | purity |
|---|---|---|---|
| 56-C10 | 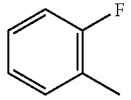 | 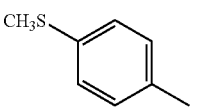 | 100% |
| 56-C13 | 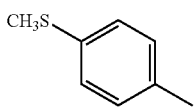 | 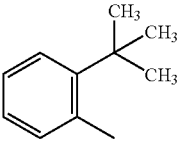 | 100% |
| 56-C14 | 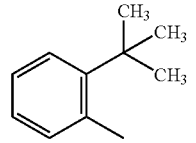 | 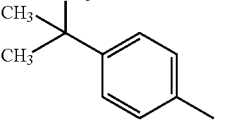 | 100% |
| 56-C15 | 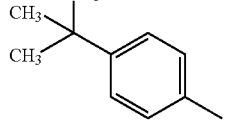 | 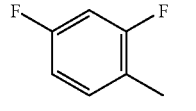 | 100% |
| 56-C16 | 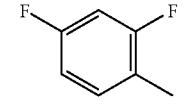 | 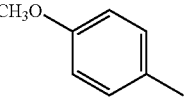 | 100% |
| 56-C18 | 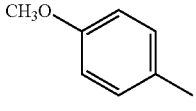 | 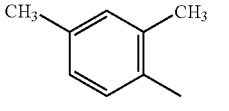 | 100% |
| 94-B2 | 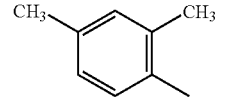 | 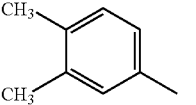 | 100% |
| 94-B3 | 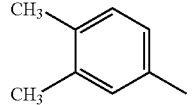 | 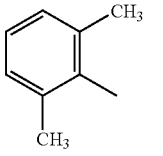 | 100% |
| 94-B4 | 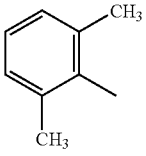 | 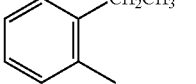 | 100% |
| 94-B5 | 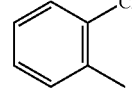 | | 100% |

TABLE 3-continued
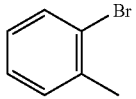
| Comp. No. | R¹ | R² | purity |
|---|---|---|---|
| 94-B6 | 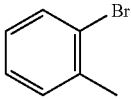 | 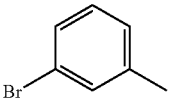 | 100% |
| 94-B7 | 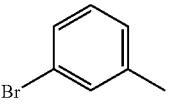 | 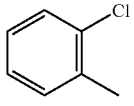 | 100% |
| 94-B8 | 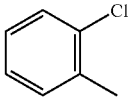 | 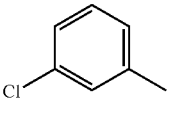 | 100% |
| 94-B9 | 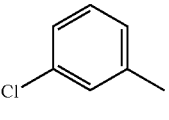 | 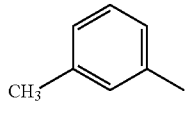 | 100% |
| 94-B10 | 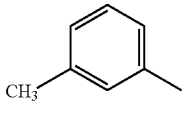 | 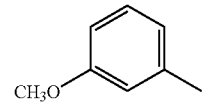 | 100% |
| 94-B11 | 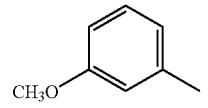 | 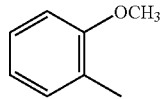 | 100% |
| 94-B12 | 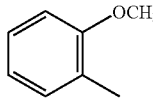 | 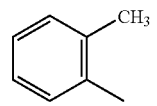 | 100% |
| 94-B13 | 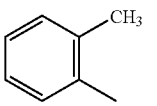 | 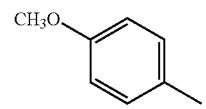 | 100% |
| 94-B14 | 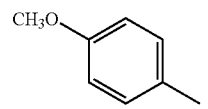 | 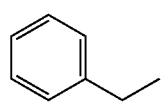 | 100% |
| 94-B16 | 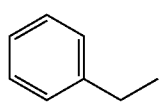 | 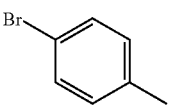 | 100% |
| 55-A1 | 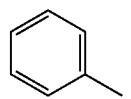 |  | 100% |

TABLE 3-continued
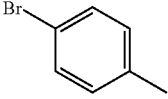
| Comp. No. | R¹ | R² | purity |
|---|---|---|---|
| 55-A2 | 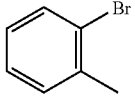 | 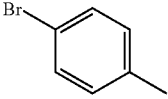 | 100% |
| 55-A3 | 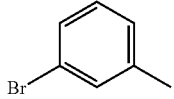 | 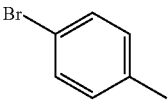 | 100% |
| 55-A5 | 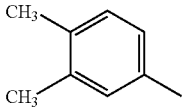 | 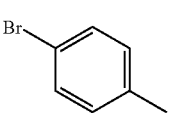 | 100% |
| 55-A6 | 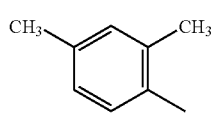 | 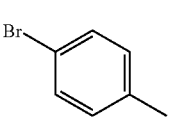 | 100% |
| 55-A7 | 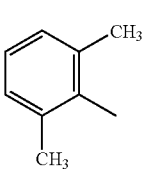 | 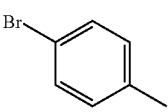 | 100% |
| 55-A8 | 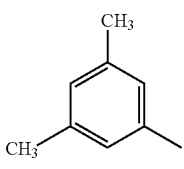 | 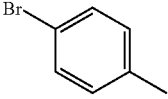 | 100% |
| 55-A9 | 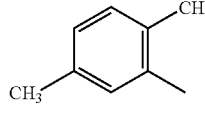 | 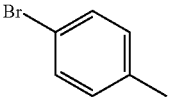 | 100% |
| 55-A10 | 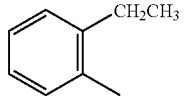 | 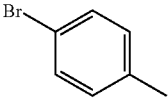 | 100% |
| 55-A11 | 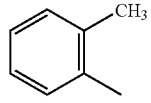 | 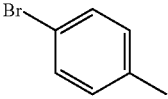 | 100% |
| 55-A12 | 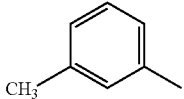 | | 100% |

TABLE 3-continued
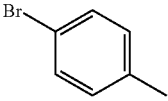
| Comp. No. | R¹ | R² | purity |
|---|---|---|---|
| 55-A13 | 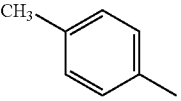 Br— | 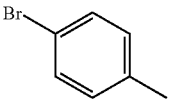 CH₃— | 100% |
| 55-A14 | 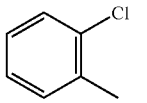 Br— | 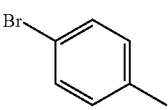 Cl | 100% |
| 55-A15 | 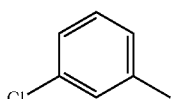 Br— | 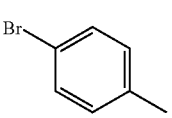 Cl | 100% |
| 55-A16 | 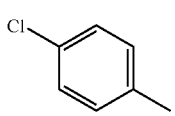 Br— | 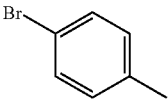 Cl— | 100% |
| 55-A17 | 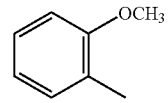 Br— | 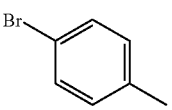 OCH₃ | 100% |
| 55-A18 | 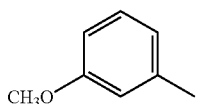 Br— | 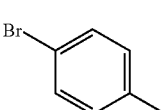 CH₃O | 100% |
| 55-A19 | 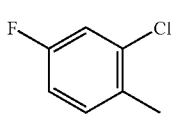 Br— | 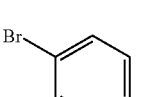 F, Cl | 100% |
| 55-A20 | 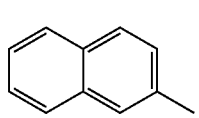 Br— | 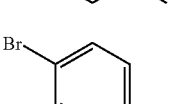 | 100% |
| 55-A21 | 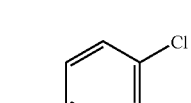 Br— | 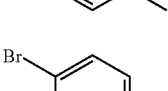 Cl, Cl | 100% |
| 55-A22 | 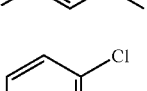 Br— | 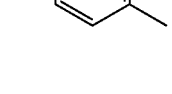 Cl, Cl | 100% |
| 55-A23 | 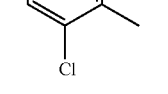 Br— | Cl, Cl | 100% |

TABLE 3-continued
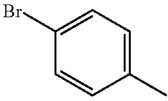
| Comp. No. | R¹ | R² | purity |
|---|---|---|---|
| 55-A24 | 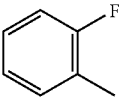 | 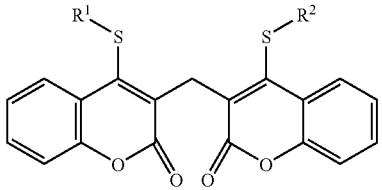 | 100% |
| 55-A25 | 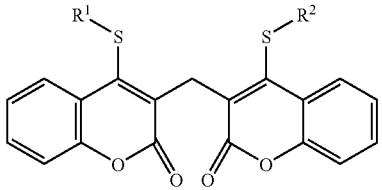 | 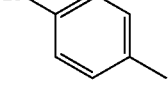 | 100% |
| 55-A26 | 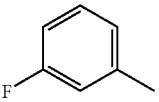 |  | 100% |
| 55-A27 |  | 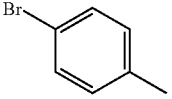 | 100% |
| 55-A28 | 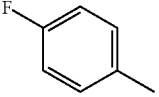 |  | 100% |
| 55-A29 |  | 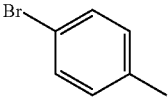 | 100% |

In another aspect of the invention, a synthetic process for the preparation of compounds of the formula I is provided. The inventive process uses mild reaction conditions, which provides a high substituent tolerance. The product is obtained in high yield and high purity. The process of the present invention is illustrated by Scheme I:

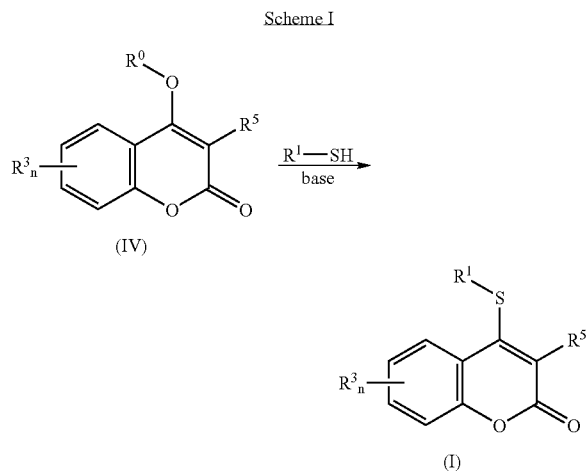

wherein $R^0$ is selected from groups that, in combination with the oxygen atom to which it is attached, forms a good leaving group which can be replaced by the thiol nucleophile. $R^0$ is preferably selected from the group consisting of aryl sulfones (tosyl, etc.) triflate, and polyhalogenated aromatic compounds. A tosyl group is particularly preferred. Preparation of compounds of the formula IV is typically from the corresponding alcohol according to procedures know in the art. For example, compounds of the formula IV may be prepared by treating the corresponding 4-hydroxycoumarin with protective group forming agent (non-limiting example includes p-toluenesulfonyl chloride), and a base in a suitable organic solvent. See Wu, J.; Liao, Y.; Yang, Z., *J. Org. Chem.* 2001, 66, 3642. 4-Hydroxycoumarins may be purchased from commercial sources or may be prepared by processes known in the art. For the general method for preparing 4-hydroxycoumarins, see (a) Laurin P.; Ferroud, D.; Klich, M.; Dupuis-Hamelin, C.; Mauvais, P.; Lassaigne, P.; Bonnefoy, A. and Musicki, B., *Bioorg. Med. Chem. Lett.* 1999, 9, 2079–2084. (b) Appendino, G.; Cravotto, G.; Giovenzana, G. B. and Palmisano, G. J., *Nat. Prod.* 1999, 62, 1627–1631.

The base employed in reaction Scheme I may be chosen from amine bases, hydroxide salts (non-limiting examples include sodium hydroxide and tetraalkylamonium hydroxides), carbonate salts, alkoxide salts (non-limiting examples include sodium methoxide and potassium t-butoxide) and the like. Preferred bases are amine bases, and particularly, the tertiary amines, such as triethylamine. The solvent may be chosen from the organic solvents known in the art that are compatible with the reaction conditions, as would be apparent to one of skill in the art. Suitable solvents may include, but are not limited to, methylene chloride, THF, toluene, dialkylethers, ketones (non-limiting examples include acetone and methyl ethyl ketone), esters (a non-limiting example includes ethyl acetate), alcohols (non-limiting examples include methanol and ethanol), acetonitrile, DMSO, DMF, and mixtures thereof. A preferred solvent is methylene chloride. 0039 The reaction is carried out under mild conditions. Preferably, the reaction is run until completion, as monitored by thin-layer chromatography, HPLC or another comparable method. The reaction temperature is preferably less than about 80° C. It is particularly preferred that the reaction be performed at room temperature (about 20–25° C.). Additionally the reaction is capable of being performed under an air atmosphere, although inert atmospheres (e.g., nitrogen, argon, etc.) may also be used. Thus, the inventive process is applicable to the preparation of a wide variety of 4-thio substituted coumarin derivatives with diverse substitution patterns. As a result, the inventive process in appropriate for use with the solid-support (solid phase) synthesis of 4-thio substituted coumarin derivatives. Thus, the inventive process provides a method for producing a library of 4-thio substituted coumarin derivatives for biological screening.

In another embodiment of the present invention, coumarin dimers are prepared from a compound of the formula V according to the reaction Scheme II:

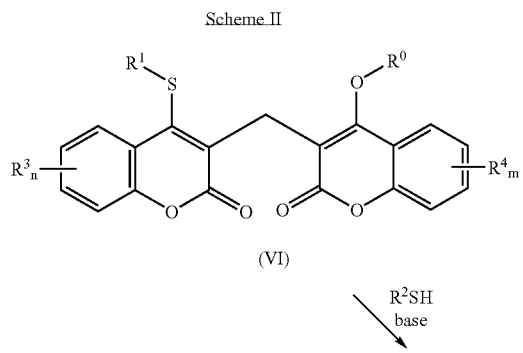

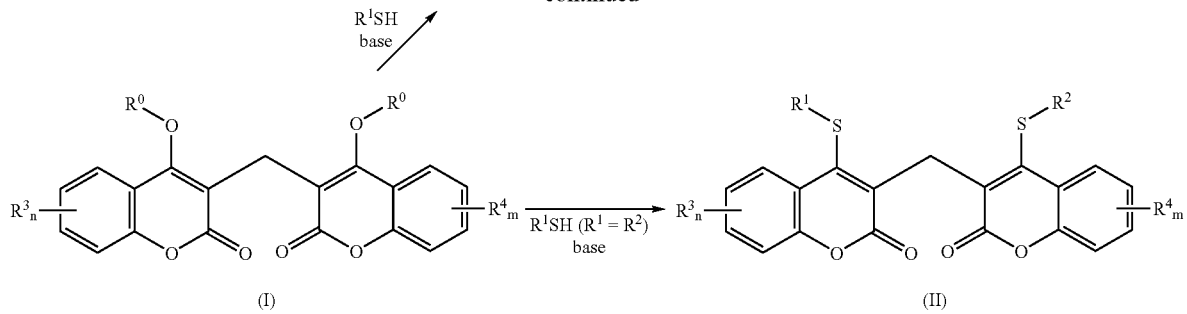

wherein R⁰, is as defines in Scheme I, and R¹, R², R³, R⁴, n and m are as defined in Formula II. The compound VI is treated with a thiol, represented by R¹SH and/or R²SH, and a base in an appropriate solvent. The base, solvent and reaction conditions are as described above for Scheme I.

As shown in Scheme II, when R¹ is the same as R², the reaction of the compound of the formula V with a thiol and base to give the product II can be carried out in a single reaction step. In another embodiment of the invention, when R¹ is not the same as R², the substitution may be carried out in two steps. Short reaction times, even in the presence of excess thiol, generally results in the mono-substituted product (VI). Longer reaction times in the presence of two or more equivalents of thiol results in the final product (II).

In one embodiment, a compound linked to a solid support, represented by the formula VII, is treated according to the process of reaction Scheme I with a thiol and a base in an appropriate solvent. The product of the substitution reaction, represented by the formula VIII, is cleaved from the solid support. This embodiment is summarized in reaction Scheme III:

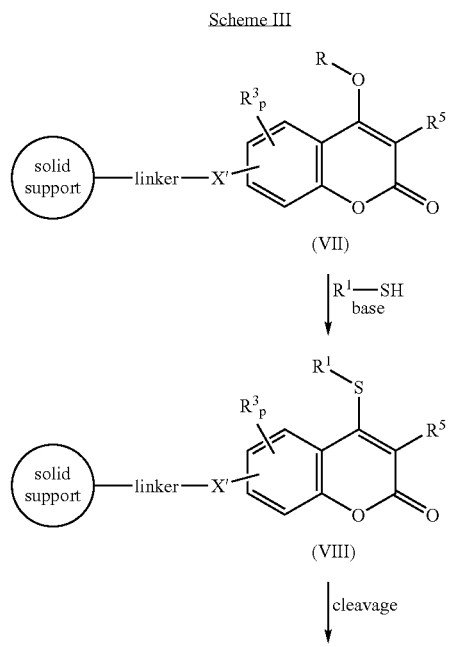

-continued

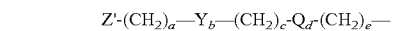

(IX)

wherein R⁰ is as defined for Scheme I, and R¹, R³ and R⁵ are as defined above for the compound of Formula I, p is selected from values between 0 and 3, X' is a selected from O, S, —O-lower alkyl- or a group of the formula $$Z'\text{-}(CH_2)_a\text{-}Y_b\text{-}(CH_2)_c\text{-}Q_d\text{-}(CH_2)_e\text{-}$$

wherein Y and Q are independently selected from an aromatic group, O, S, —CR=CR—,

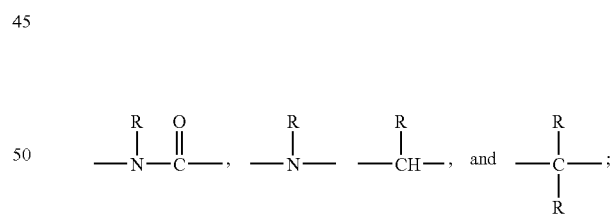

each R is independently selected from H or lower alkyl,

Z' is selected from O, S, CO₂, NR,

—NHCO—, and —NHC(=O)—CH₂O—;

a, c and e are independently selected from values from 0 to 10; and b and d are independently selected from 0 and 1, provided that when a=0 then b=0, and when c=0 then d=0.

X is the chemical group that results from the cleavage of X' and linker. Thus, for example, if X' is O, then X may be HO— after cleavage, and if X' is —O-lower alkyl-, then X may be HO— lower alkyl after cleavage. More generally, when X' is selected from a group of the formula Z'-$(CH_2)_a$—$Y_b$—$(CH_2)_c$-$Q_d$-$(CH_2)_e$—, then X may be a group of the formula HZ'-$(CH_2)_a$—$Y_b$—$(CH_2)_c$-$Q_d$-$(CH_2)_e$—.

The solid support is an insoluble, functionalized, polymeric material to which library members or reagents may be attached via a linker, allowing them to be readily separated (by filtration, centriftigation, etc.) from excess reagents, soluble reaction by-products, or solvents. The solid support is chosen from the solid support materials known in the art, e.g., commercially available resins used for solid phase synthesis in combinatorial chemistry or in solid phase peptide synthesis. For example, the solid support may be chosen from cross-linked polystyrene resins, polystyrene/DVB-polyethylene resins (for example, TentaGel resin, ArgoGel, etc.), controlled-pore glass and Kieselguhr/polyacrylamide. A preferred solid support is a high-capacity polystyrene macrobead.

The linker is a chemical moiety that provides a means of attachment for the immobilized chemical reagent to the solid support. The linker may be any chemical component capable of being selectively cleaved to release a compound of the formula IX from the solid support. Yields for the loading and cleavage to the linker should be as quantitative as possible. The linker may be chosen from those customarily used in the art that are stable to the reactions conditions. Examples of suitable linkers may be found in the review by Guillier et al., *Chem. Rev.* 2000, 100, 2019–2157. Preferred linkers are silyl based linkers, for example the silyl based linkers disclosed in Sternson et al., *J. Am. Chem. Soc.* 2001, 123, 1740–1747, Blackwell et al., *Org. Lett.* 2001, 3, 1185–1188, Pelish et al., *J. Am. Chem. Soc.* 2001, 123, 6740–6741, and Tallarico et al., *J. Comb. Chem.* 2001, 3, 312–318, and the like.

A preferred method of generating a 4-thio substituted coumarin library using the process of the present invention is to employ silyl linker-based high capacity macrobeads as a solid support in order to realize a "one bead, one compound" concept. These beads have a high-capacity (up to about 4 mmol/g) and provide sufficient material from a single bead for multiple assays. The silyl linker allows compounds generated on the beads to be released utilizing volatile cleavage reagents (such as HF/pyridine or trimethylsilyl-methanol) so that the compounds can go directly into biological assays without further purification. The purity of the products, as determined by LC-MS, is very high, often exceeding 90%, and in some cases >99% purity was obtained.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

In another embodiment of the present invention, compounds of the formula XI are prepared according to the reaction Scheme IV:

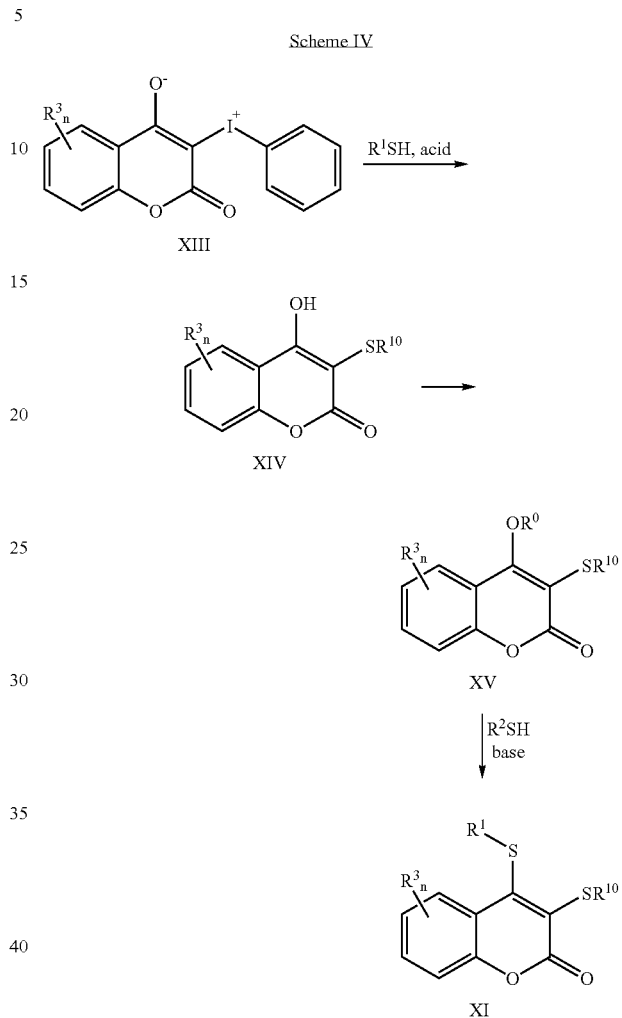

wherein $R^0$ is selected from groups that, in combination with the oxygen atom to which it is attached, forms a good leaving group which can be replaced by the thiol nucleophile. $R^0$ is preferably selected from the group consisting of aryl sulfones (tosyl, etc.) triflate, and polyhalogenated aromatic compounds. Preparation of compounds of the formula XIII is typically from the corresponding 4-hydroxycoumarin, for example by treatment with iodobenzene diacetate and base (i.e., $Na_2CO_3$, etc.) in water or other suitable solvent. 0049 The acid employed in the first step of Scheme IV may be selected from any suitable acid, including mineral acids and organic acids. A preferred acid is trifluoroacetic acid. The base employed in the third step of Scheme IV may be chosen from amine bases, hydroxide salts (non-limiting examples include sodium hydroxide and tetraalkylammonium hydroxides), carbonate salts, alkoxide salts (non-limiting examples include sodium methoxide and potassium t-butoxide) and the like. Preferred bases are amine bases, and particularly, the tertiary amines, such as triethylamine. The solvent may be chosen from the organic solvents known in the art that are compatible with the reaction conditions, as would be apparent to one of skill in the art. Suitable solvents may include, but are not limited to, methylene chloride, THF, toluene, dialkylethers, ketones (non-limiting examples include acetone and methyl ethyl ketone), esters (a non-limiting example includes ethyl acetate), alcohols (non-limiting examples include methanol and ethanol), acetonitrile, DMSO, DMF, and mixtures thereof. A preferred solvent is methylene chloride. The reactions are carried out under mild conditions. Preferably, the reactions are run until completion, as monitored by thin-layer chromatography, HPLC or another comparable method. The reaction temperatures are preferably less than about 80° C. It is particularly preferred that the reactions be performed at room temperature (about 20–25° C.).

The compounds and processes disclosed herein are useful in the production of a library of 4-thio substituted coumarin derivatives for biological screening. Derivatives of coumarin posses a range of biological activities. Coumarin-based compounds have shown efficacy, for example, as anticoagulants, antifungals, and antivirals. Particularly, the compounds of the present invention may be used to prevent or treat infection with HCV.

Thus, In another embodiment, the present invention provides pharmaceutical compositions comprising an anti-HCV effective amount of a compound of formula I, or a pharmaceutically acceptable salt or hydrate thereof, in combination with a pharmaceutically acceptable carrier or auxiliary agent. As used herein, the terms "pharmaceutically acceptable salts" and "hydrates" refer to those salts and hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity and flowability of the resulting bulk drug.

The invention also provides a method of treating HCV infection in a mammal by administering to the mammal an effective amount of a compound of formula I, a pharmaceutically acceptable salt or hydrate thereof, or a composition as described above, alone or in combination with one or more of: interferon (pegylated or not), or ribavirin, or one or more other anti-HCV agents, administered together or separately, e.g., prior to, concurrently with or following the administration of the compound of formula I or pharmaceutically acceptable salt thereof. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

The compounds of the present invention may be employed in solid or liquid form including, for example, amorphous powder or crystalline form, in solution or in suspension. They may be administered in numerous different ways, such as orally, parenterally, topically, transdermally or by inhalation. Oral administration or administration by injection is preferred. The choice of carrier and the content of active compound in the carrier are generally determined in accordance with the solubility and chemical properties of the desired product, the particular mode of administration and well established pharmaceutical practice. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrastemal, intrathecal, and intralesional injection or infusion techniques.

Examples of liquid carriers include syrups, peanut oil, olive oil, water, saline and the like. For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, may be used. Injectable forms must be fluid to the extent they can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. Compounds of the invention may be enclosed in hard or soft shell gelatin capsules, or compressed into tablets. Examples of oral liquid dosage forms include solutions, suspensions, syrups, emulsions, soft gelatin capsules and the like. Carriers for oral use (solid or liquid) may include time delay materials known in the art, such as glyceryl monostearate or glyceryl distearate alone or with a wax. To prepare a capsule, it may be advantageous to use lactose and a liquid carrier, such as high molecular weight polyethylene glycols.

Compositions and dosage forms prepared in accordance with the present invention optionally may contain lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, capsules and the like. Various other materials may be present as coatings or to otherwise modify the physical form of the dosage unit. For instance, tablets, and capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, and mixtures thereof also may be used. In addition, the active compound may be incorporated into sustained-release preparations and formulations. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", The Science and Practice of Pharmacy, 19.sup.th Ed. Mack Publishing Company, Easton, Pa., (1995).

When these compounds or their pharmaceutically acceptable salts are formulated together with a pharmaceutically acceptable carrier, the resulting composition may be administered in vivo to mammals, such as man, to treat or prevent HCV virus infection. Such treatment may also be achieved using a compound of this invention in combination with other anti-viral agents which include, but are not limited to a-interferon and ribavirin. The additional agents may be combined with compounds of this invention to create a single dosage form. Alternatively these additional agents may be separately administered to a mammal as part of a multiple dosage form.

EXAMPLES

In the illustrative examples set forth herein, the following general methods, apparatus and material may be employed. It should be noted that when purities of 100% are reported, the products are pure to the limit of detection for the analysis used.

Materials: Reaction solvents were commercially purchased from Acros and Aldrich without further purification and reagents were used as received. Flash column chromatography was performed on Merck Silica Gel 60 (230–400 mesh) using reagent grade hexanes, dichloromethane, methanol and ethyl acetate.

Process for the Preparation of Dicumarol Starting Materials

The representative process described below in Scheme V may be expanded for use in preparing a wide variety of dicumarol derivatives. See Appendino, G.; Cravotto, G.; Giovenzana, G. B. and Palmisano, G. J., *Nat. Prod.* 1999, 62, 1627–1631.

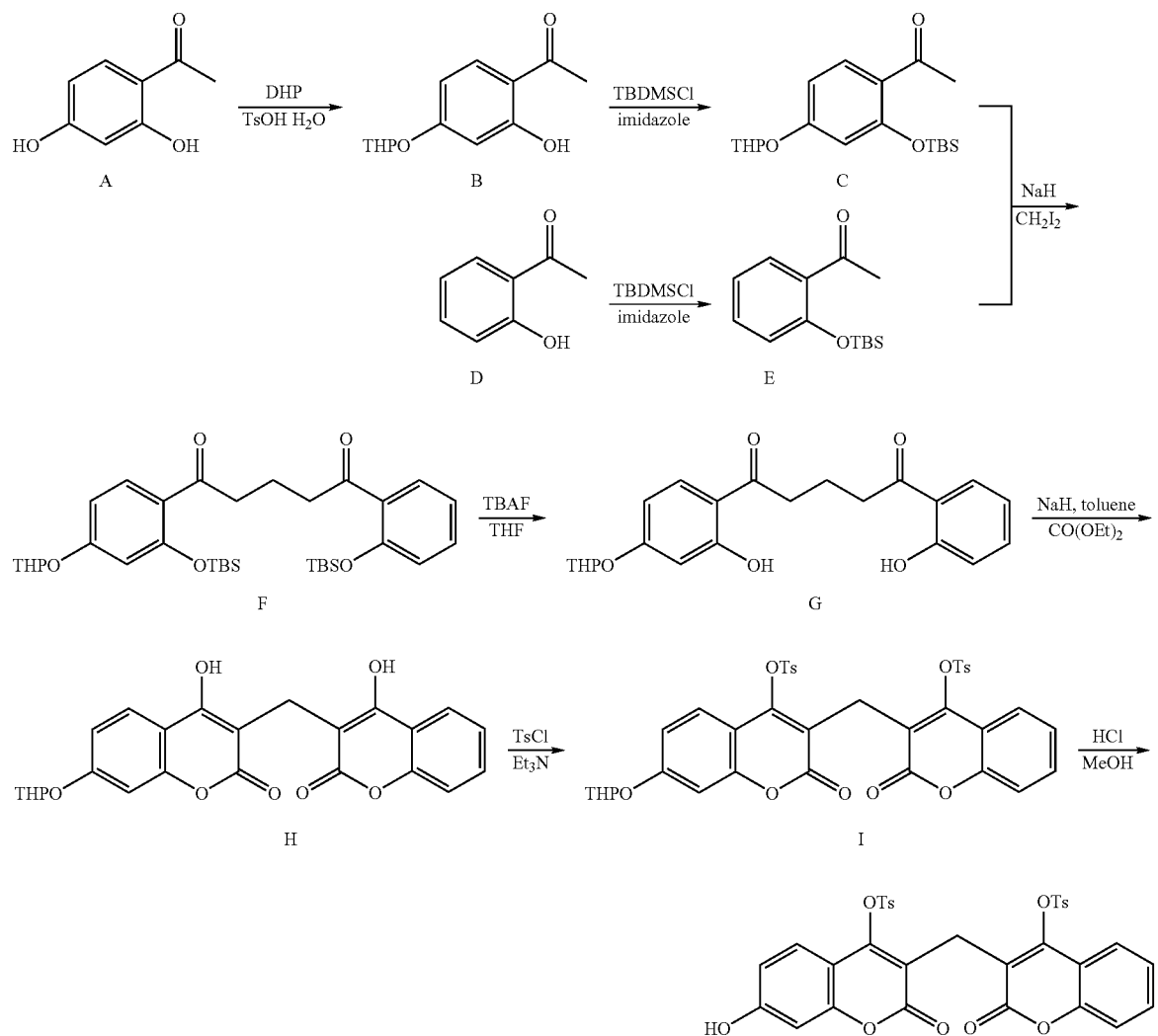

Synthetic Procedure:

From A to B:

To a solution of compound A (1.0 eq.) and TsOH.H₂O (cat.) in ether, 3,4-dihydroxy-2H-pyran (DHP) (5.0 eq.) was added at room temperature. After the reaction was completed, the mixture was evaporated and the residue was purified by flash chromatography (silica gel) to afford the corresponding product B.

From B to C:

To a solution of compound B (1.0 eq.) and imidazole (1.1 eq.) in dichloromethane, tert-butyldimethylsilyl chloride (1.1 eq.) was added at room temperature. After the reaction was completed, the mixture was filtered and the filtrate was evaporated and the residue was purified by flash chromatography (silica gel) to afford the corresponding product C.

From D to E:

To a solution of compound D (1.0 eq.) and imidazole (1.1 eq.) in dichloromethane, tert-butyldimethylsilyl chloride (1.1 eq.) was added at room temperature. After the reaction was completed, the mixture was filtered and the filtrate was evaporated and the residue was purified by flash chromatography (silica gel) to afford the corresponding product E.

From C, E to F.:

To a solution of compound C (1.0 eq.), E (1.0 eq) and sodium hydride (2.4 eq.) in toluene, diiodomethane (1.1 eq.) was added at room temperature. The reaction was stirred under reflux. After the reaction was completed, the mixture was filtered and the filtrate was evaporated and the residue was purified by flash chromatography (silica gel) to afford the corresponding product F.

From F to G:

To a solution of compound F (1.0 eq.) in THF, tetrabutylammonium fluoride (1.0 M in THF) (1.2 eq) was added at room temperature. After the reaction was completed, the mixture was evaporated and the residue was purified by flash chromatography (silica gel) to afford the corresponding product G.

From G to H:

To a solution of compound G (1.0 eq.) and sodium hydride (2.4 eq.) in toluene, CO(OEt)₂ (1.2 eq.) was added at room temperature. The reaction was stirred under reflux overnight. After the reaction was completed, the mixture was washed with water. The inorganic phase was separated and evaporated. The compound H was obtained as solid and directly used in the next step without further purification.

From H to I:

To a solution of compound H (1.0 eq.) and p-toluenesulfonyl chloride (1.1 eq.) in dichloromethane, triethylamine (1.5 eq.) was added at room temperature. After the reaction was completed, the mixture was filtered and the filtrate was evaporated. The residue was purified by flash chromatography (silica gel) to afford the corresponding product I.

From I to 10:

To a solution of compound I (1.0 eq.) in methanol, HCl (3.0 M in water) was added at room temperature. After the reaction was completed, the mixture was separated and extracted with ethyl acetate. The organic phase was combined and washed with brine. After dried in Na₂SO₄, the solvent was removed and the residue was purified by flash chromatography (silica gel) to afford the corresponding product 10.

¹H (300M Hz, CDCl₃): δ 2.40 (s, 6H), 2.65 (s, 2H), 6.70 (m, 2H), 7.20–7.60 (m, 9H), 7.70–7.80 (m, 4H), 10.10 (s, 1H).

Example 1

To a solution of dicumarol (10 mmol) and p-toluenesulfonyl chloride (1.0 eq.) in dichloromethane (20 ml), triethylamine was added at room temperature under air atmosphere. After the reaction was complete, as monitored by TLC, the reaction mixture was evaporated and the residue was purified by flash chromatography (silica gel) to afford the product, 3,3'-methylenebis[4-tosylcoumarin].

Example 2

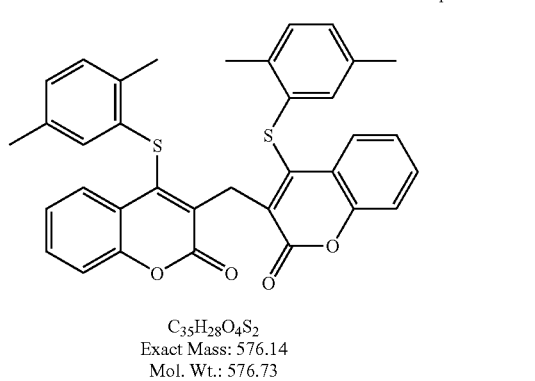

Compound 56-C3

C₃₅H₂₈O₄S₂
Exact Mass: 576.14
Mol. Wt.: 576.73

To a solution of 3,3'-methylenebis[4-tosylcoumarin] (1.0 mmol) and 2,5-dimethylbenzenethiol (2.0 eq.) in dichloromethane (5 mL), triethylamine (3.0 eq.) was added at room temperature under air atmosphere. After the reaction was complete as monitored by thin-layer chromatography (TLC), the mixture was evaporated and the residue was purified by flash chromatography (silica gel) to afford the corresponding product 56-C3. >99% yield, 100% pure.

¹H NMR (500 MHz/CDCl₃): δ (ppm): 2.07 (s, 6H), 2.39 (s, 6H), 4.56 (s, 2H), 6.48 (s, 2H), 6.68 (d, J=7.5 Hz, 2H), 6.89 (d, J=7.5 Hz, 2H), 7.09–7.12 (m, 2H), 7.26 (d, J=5.5 Hz, 2H), 7.39–7.41 (m, 2H), 7.68 (dd, J=8.5, 1.5 Hz, 2H).

Example 3

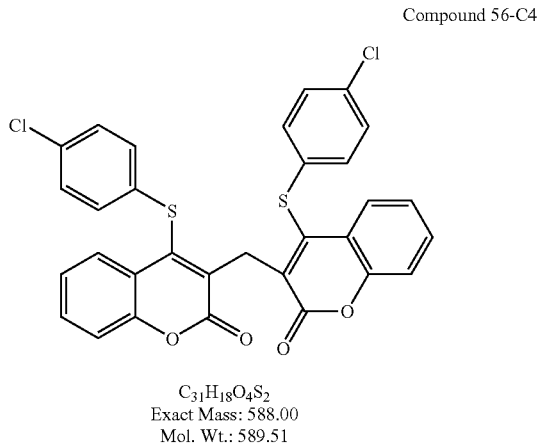

Compound 56-C4

C₃₁H₁₈O₄S₂
Exact Mass: 588.00
Mol. Wt.: 589.51

To a solution of 3,3'-methylenebis[4-tosylcoumarin] (1.0 mmol) and 4-chlorobenzenethiol (2.0 eq.) in dichloromethane (5 mL), triethylamine (3.0 eq.) was added at room temperature under air atmosphere. After the reaction was complete as monitored by TLC, the mixture was evaporated and the residue was purified by flash chromatography (silica gel) to afford the corresponding product 56-C4. >99% yield, 100% pure.

$^1$H NMR (500 MHz/CDCl$_3$): δ (ppm): 4.69 (s, 2H), 7.06 (d, J=6.0 Hz, 4H), 7.07–7.13 (m, 4H), 7.27–7.29 (m, 4H), 7.43–7.45 (m, 2H), 7.73 (dd, J=8.5, 1.5 Hz, 2H).

Example 4

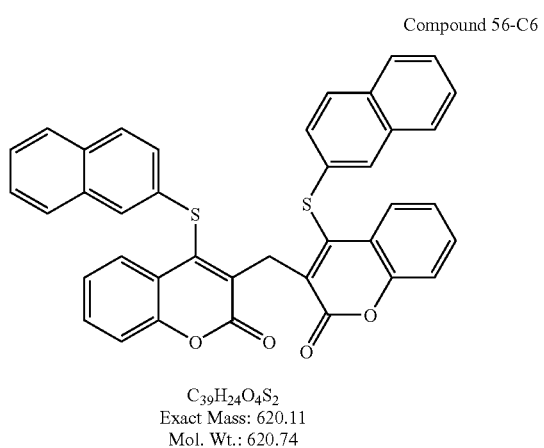

Compound 56-C6

C$_{39}$H$_{24}$O$_4$S$_2$
Exact Mass: 620.11
Mol. Wt.: 620.74

To a solution of 3,3'-methylenebis[4-tosylcoumarin] (1.0 mmol) and 2-naphthylenethiol (2.0 eq.) in dichloromethane (5 mL), triethylamine (3.0 eq.) was added at room temperature under air atmosphere. After the reaction was complete as monitored by TLC, the mixture was evaporated and the residue was purified by flash chromatography (silica gel) to afford the corresponding product 56-C6. >99% yield, 100% pure.

$^1$H NMR (500 MHz/CDCl$_3$): δ (ppm): 4.76 (s, 2H), 6.98 (t, 2H), 7.15–7.19 (m, 4H), 7.26–7.42 (m, 6H), 7.51 (d, J=1.5 Hz, 2H), 7.56–7.75 (m, 6H), 7.76 (d, J=1.5 Hz, 2H).

Example 5

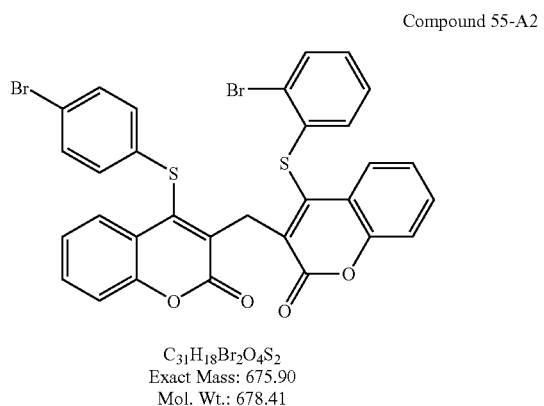

Compound 55-A2

C$_{31}$H$_{18}$Br$_2$O$_4$S$_2$
Exact Mass: 675.90
Mol. Wt.: 678.41

To a solution of 3,3'-methylenebis[4-tosylcoumarin] (1.0 mmol) and 4-bromobenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product. To a solution of the product 2-bromobenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product 55-A2. >99% yield, 100% pure.

$^1$H NMR (500 MHz/CDCl$_3$): δ (ppm): 4.66 (s, 2H), 6.70–6.75 (m, 1H), 6.80–6.90 (m, 1H), 6.90–7.02 (m, 2H), 7.14–7.17 (m, 2H), 7.25–7.32 (m, 4H), 7.38–7.47 (m, 4H), 7.69–7.78 (m, 2H).

Example 26

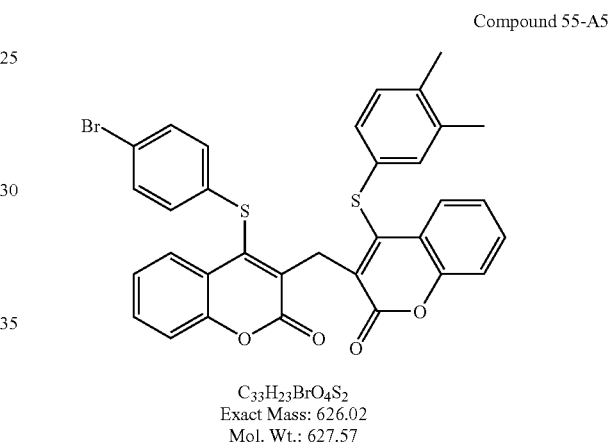

Compound 55-A5

C$_{33}$H$_{23}$BrO$_4$S$_2$
Exact Mass: 626.02
Mol. Wt.: 627.57

To a solution of 3,3'-methylenebis[4-tosylcoumarin] (1.0 mmol) and 4-bromobenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product. To a solution of the product and 3,4-dimethylbenzenethiol (1.0 eq.) in dichloromethane (5 mL), triethylamine (1.5 eq.) was added at room temperature under air atmosphere. After the reaction was complete as monitored by TLC, the mixture was evaporated and the residue was purified by flash chromatography (silica gel) to afford the corresponding product 55-A5.

Example 7

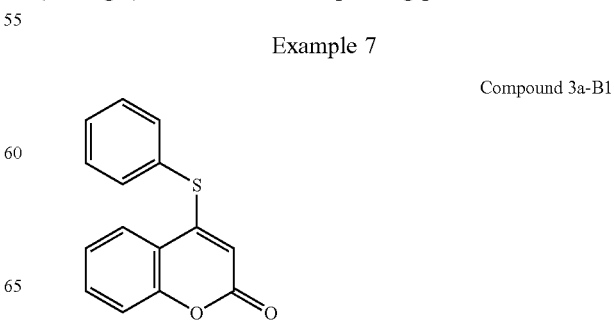

Compound 3a-B1

Benzenethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B1. 99% yield as colorless oil. 100% pure.

$^1$H NMR (500 MHz, CDCl$_3$) δ (ppm) 5.67 (s, 1H), 7.33–7.38 (m, 2H), 7.50–7.63 (m, 6H), 7.88 (d, J=8.0 Hz, 1H). $^{13}$C NMR (125.7 MHz) δ (ppm) 159.79, 158.17, 152.50, 136.38, 132.57, 131.16, 130.69, 126.45, 124.41, 123.95, 118.08, 117.47, 108.64. MS (APCI) [C$_{15}$H$_{10}$O$_2$S], m/z (M$^+$+1): calcd 255, found 255.

Example 8

Compound 3a-B5

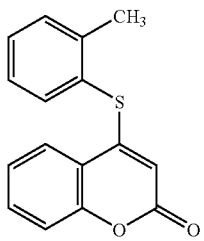

2-methylbenzenethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B5. 97% yield as colorless oil. 100% pure.

$^1$H NMR (500 MHz, CDCl$_3$) δ (ppm) 2.45 (s, 3H), 5.52 (s, 1H), 7.31–7.50 (m, 5H), 7.57–7.63 (m, 2H), 7.92 (d, J=8.0 Hz, 1H). $^{13}$C NMR (125.7 MHz) δ (ppm) 159.79, 157.06, 152.58, 143.70, 137.44, 132.52, 131.97, 131.75, 128.12, 125.62, 124.41, 124.13, 118.15, 117.46, 107.87, 20.73. MS (APCI) [C$_{16}$H$_{12}$O$_2$S], m/Z (M$^+$+1): calcd 269, found 269.

Example 9

Compound 3a-B10

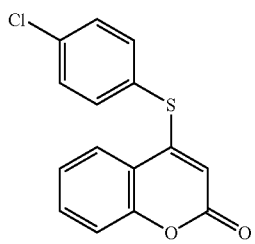

4-chlorobenzenethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B10. 98% yield as colorless oil. 100% pure.

$^1$H NMR (500 MHz, CDCl$_3$) δ (ppm) 5.63 (s, 1H), 7.31–7.38 (m, 2H), 7.48–7.62 (m, 5H), 7.83 (d, J=8.0 Hz, 1H). $^{13}$C NMR (125.7 MHz) δ (ppm) 159.55, 157.52, 152.48, 137.89, 137.58, 132.73, 131.00, 124.88, 124.49, 123.88, 117.87, 117.49, 108.78. MS (APCI) [C$_{15}$H$_9$ClO$_2$S], m/z (M$^+$+1): calcd 289, found 289.

Example 10

Compound 3a-C7

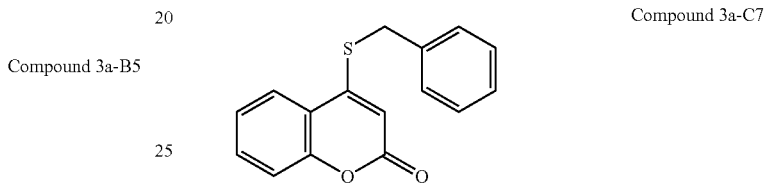

Benzylthiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C7. 57% yield as colorless oil. 100% pure.

$^1$H NMR (500 MHz, CDCl$_3$) δ (ppm) 4.28 (s, 2H), 6.25 (s, 1H), 7.25–7.47 (m, 7H), 7.56 (t, J=8.0, 7.0 Hz, 1H), 7.74 (d, J=8.0 Hz, 1H). $^{13}$C NMR (125.7 MHz) δ (ppm) 159.45, 156.31, 152.42, 133.97, 132.45, 129.31, 129.23, 128.50, 124.36, 124.03, 118.23, 117.49, 107.62, 36.02. MS (APCI) [C$_{16}$H$_{12}$O$_2$S], m/z (M$^+$+1): calcd 269, found 269.

Example 11

Compound 3a-C10

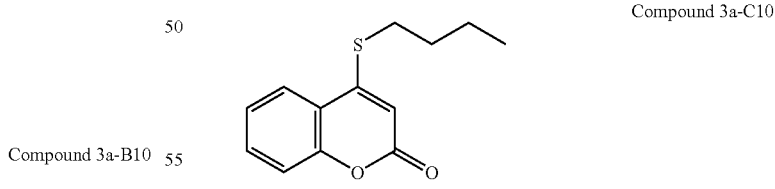

1-Butanethiol (0.30 mmol, 1.2 equiv.) was added to a solution of 4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C10. 68% yield as colorless oil. 100% pure.

¹H NMR (500 MHz, CDCl₃) δ (ppm) 1.00 (t, J=7.5 Hz, 3H), 1.50–1.60 (m, 2H), 1.75–1.85 (m, 2H), 3.03 (t, J=7.5 Hz, 2H), 6.16 (s, 1H), 7.26–7.50 (m, 2H), 7.55 (dt, J=8.5, 1.5 Hz, 1H), 7.76 (dd, J=8.0, 1.5 Hz, 1H). ¹³C NMR (125.7 MHz) δ (ppm) 159.64, 156.98, 152.38, 132.33, 124.29, 124.11, 118.50, 117.44, 106.94, 30.80, 29.90, 22.40, 13.79. MS (APCI) [$C_{13}H_{14}O_2S$], m/z (M⁺+1): calcd 235, found 235.

Example 12

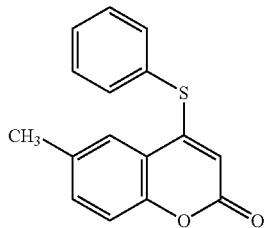

Compound 3b-B1

Benzenethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B1. 94% yield as colorless oil. 100% pure.

¹H NMR (500 MHz, CDCl₃) δ (ppm) 2.48 (s, 3H), 5.64 (s, 1H), 7.25 (d, J=8.0 Hz, 1H), 7.40 (dd, J=8.5, 1.5 Hz, 1H), 7.50–7.65 (m, 6H). ¹³C NMR (125.7 MHz) δ (ppm) 160.03, 158.00 150.58, 136.39, 134.18, 133.58, 131.11, 130.66, 126.57, 123.70, 117.74, 117.17, 108.54, 21.20. MS (APCI) [$C_{16}H_{12}O_2S$], m/z (M⁺+1): calcd 269, found 269.

Example 13

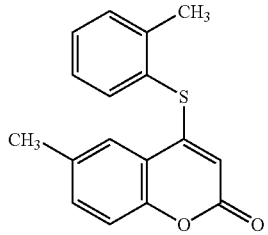

Compound 3b-B5

2-Methylbenzenethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B5. 99% yield as colorless oil. 100% pure.

¹H NMR (500 MHz, CDCl₃) δ (ppm) 2.44 (s, 3H), 2.48 (s, 3H), 5.49 (s, 1H), 7.24–7.50 (m, 5H), 7.58 (d, J=7.5 Hz, 1H), 7.69 (s, 1H). ¹³C NMR (125.7 MHz) δ (ppm) 160.03, 156.89, 150.67, 143.69, 137.46, 134.18, 133.52, 131.95, 131.70, 128.10, 125.74, 123.89, 117.81, 117.18, 107.78, 21.20, 20.73. MS (APCI) [$C_{17}H_{14}O_2S$], m/z (M₊+1): calcd 283, found 283.

Example 14

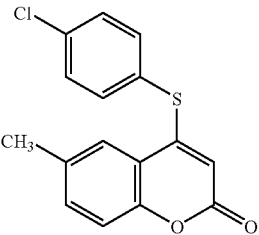

Compound 3a-B10

4–Chloro-benzenethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-B10. 97% yield as colorless oil. 100% pure.

¹H NMR (500 MHz, CDCl₃) δ (ppm) 2.47 (s, 3H), 5.61 (s, 1H), 7.22–7.28 (m, 1H), 7.37–7.42 (m, 1H), 7.49–7.64 (m, 5H). ¹³C NMR (125.7 MHz) δ (ppm) 159.80, 157.37, 150.58, 137.85, 137.60, 134.27, 133.73, 130.97, 125.00, 123.63, 117.55, 117.21, 108.69, 21.20. MS (APCI) [$C_{16}H_{11}ClO_2S$], m/z (M⁺+1): calcd 303, found 303.

Example 15

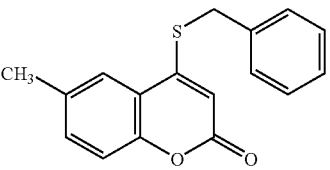

Compound 3a-C7

Benzylthiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C7. 64% yield as colorless oil. 100% pure.

¹H NMR (500 MHz, CDCl₃) δ (ppm) 2.40 (s, 3H), 4.26 (s, 2H), 6.22 (s, 1H), 7.22 (d, J=8.0 Hz, 1H), 7.33–7.47 (m, 6H), 7.51 (s, 1H). $^{13}$C NMR (125.7 MHz) δ (ppm) 159.69, 156.15, 150.51, 134.10, 134.03, 133.43, 129.30, 129.24, 128.48, 123.82, 117.88, 117.19, 107.51, 36.00, 21.13. MS (APCI) [$C_{17}H_{14}O_2S$], m/z (M$^+$+1): calcd 283, found 283.

Example 16

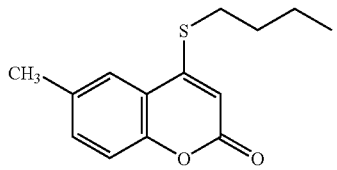

Compound 3a-C10

1-Butanethiol (0.30 mmol, 1.2 equiv.) was added to a solution of 6-methyl-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3a-C10. 63% yield as colorless oil. 100% pure.

$^1$H NMR (500 MHz, CDCl$_3$) δ (ppm) 1.00 (dt, J=7.0, 2.0 Hz, 3H), 1.52–1.60 (m, 2H), 1.76–1.86 (m, 2H), 2.42 (s, 3H), 3.02 (dt, J=7.0, 2.0 Hz, 2H), 6.14 (s, 1H), 7.22 (dd, J=8.5, 2.0 Hz, 1H), 7.34 (d, J=8.5 Hz, 1H), 7.53 (s, 1H). $^{13}$C NMR (125.7 MHz) δ (ppm) 159.89, 156.81, 150.47, 134.02, 133.33, 123.88, 118.15, 117.15, 106.87, 30.78, 29.90, 22.39, 21.15, 13.79. MS (APCI) [$C_{14}H_{16}O_2S$], m/z (M$^+$+1): calcd 249, found 249.

Example 17

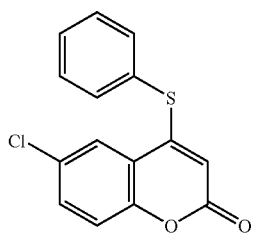

Compound 3c-B1

Benzenethiol (0.30 mmol, 1.2 equiv.) was added to a solution of 6-chloro-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3c-B1. 96% yield as colorless oil. 100% pure.

$^1$H NMR (500 MHz, CDCl$_3$) δ (ppm) 5.68 (s, 1H), 7.30 (d, J=8.5 Hz, 1H), 7.52–7.62 (m, 6H), 7.84 (d, J=2.5 Hz, 1H). $^{13}$C NMR (125.7 MHz) δ (ppm) 159.11, 157.07, 150.94, 136.35, 132.51, 131.37, 130.81, 129.92, 125.96, 123.61, 119.14, 118.85, 109.39. MS (APCI) [$C_{15}H_9ClO_2S$], m/z (M$^+$+1): calcd 289, found 289.

Example 18

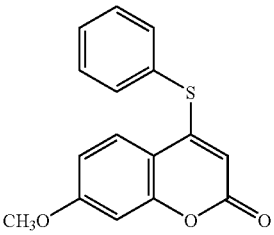

Compound 3d-B1

Benzenethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-B1. 99% yield as colorless oil. 100% pure.

$^1$H NMR (500 MHz, CDCl$_3$) δ (ppm) 3.90 (s, 3H), 5.51 (s, 1H), 6.82 (d, J=2.5 Hz, 1H), 6.90 (dd, J=9.0, 2.5 Hz, 1H), 7.49–7.60 (m, 3H), 7.60 (dd, J=7.5, 1.5 Hz, 2H), 7.75 (d, J=9.0 Hz, 1H). $^{13}$C NMR (125.7 MHz) δ (ppm) 163.33, 160.20, 158.17, 154.33, 136.38, 131.03, 130.58, 126.59, 124.99, 112.57, 111.62, 105.65, 101.04, 56.05. MS (APCI) [$C_{16}H_{12}O_3S$], m/z (M$^+$+1): calcd 285, found 285.

Example 19

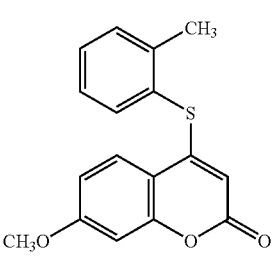

Compound 3d-B5

2-methylbenzenethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-B5. 95% yield as colorless oil. 100% pure.

$^1$H NMR (500 MHz, CDCl$_3$) δ (ppm) 2.43 (s, 3H), 3.90 (s, 3H), 5.36 (s, 1H), 6.82 (d, J=2.5 Hz, 1H), 6.90 (dd, J=8.5, 2.5 Hz, 1H), 7.29–7.34 (m, 1H), 7.39–7.48 (m, 2H), 7.57 (d, J=7.5 Hz, 1H), 7.79 (d, J=9.0 Hz, 1H). $^{13}$C NMR (125.7 MHz) δ (ppm) 163.30, 160.22, 157.12, 154.42, 143.70, 137.46, 131.89, 131.64, 128.01, 125.77, 125.15, 112.58, 111.70, 104.89, 101.06, 56.07, 20.75. MS (APCI) [C$_{17}$H$_{14}$O$_3$S], m/z (M$^+$+1): calcd 299, found 299.

Example 20

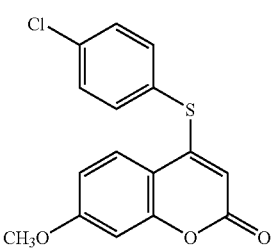

Compound 3d-B10

4-Chlorobenzenethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-B10. 96% yield as colorless oil. 100% pure.

$^1$H NMR (500 MHz, CDCl$_3$) δ (ppm) 3.89 (s, 3H), 5.47 (s, 1H), 6.81 (d, J=2.0 Hz, 1H), 6.89 (dd, J=9.0, 2.5 Hz, 1H), 7.47–7.54 (m, 4H), 7.70 (d, J=9.0 Hz, 1H). $^{13}$C NMR (125.7 MHz) δ (ppm) 163.44, 159.98, 157.51, 154.35, 137.75, 137.57, 130.88, 125.05, 124.91, 112.65, 111.42, 105.78, 101.07, 56.08. MS (APCI) [C$_{16}$H$_{11}$ClO$_3$S], m/z (M$^+$+1): calcd 319, found 319.

Example 21

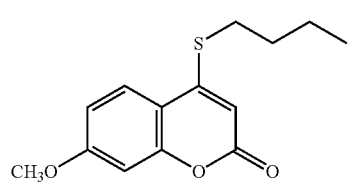

Compound 3d-C10

Butanethiol (0.30 mmol, 1.2 equiv.) was added to a solution of 7-methoxy-4-tosylatecoumarin (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product 3d-C10. 60% yield as colorless oil. 100% pure.

$^1$H NMR (500 MHz, CDCl$_3$) δ (ppm) 1.00 (t, J=7.5 Hz, 3H), 1.51–1.57 (m, 2H), 1.76–1.82 (m, 2H), 3.01 (t, J=7.5 Hz, 2H), 3.88 (s, 3H), 6.02 (s, 1H), 6.80 (d, J=2.5 Hz, 1H), 6.84 (dd, J=9.0, 2.5 Hz, 1H), 7.64 (d, J=8.5 Hz, 1H). $^{13}$C NMR (125.7 MHz) δ (ppm) 163.15, 160.08, 157.07, 154.20, 125.15, 112.48, 112.07, 104.02, 100.99, 56.01, 30.72, 30.01, 22.39, 13.79. MS (APCI) [C$_{14}$H$_{16}$O$_3$S], m/z (M$^+$+1): calcd 265, found 265.

Example 22

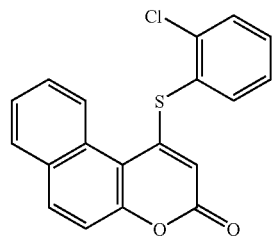

Compound 877

2-Chlorobenzenethiol (0.30 mmol, 1.2 equiv.) was added to a solution of 4-(p-toluenesulfonyloxy)-naphtho[1,2-e]pyran-2-one (0.25 mmol) and triethylamine (0.60 mmol, 2.4 equiv.) in dichloromethane (3.0 mL) under air atmosphere. The reaction mixture was stirred at room temperature. Following completion of the reaction as monitored by TLC, the reaction mixture was diluted with dichloromethane (10 mL), and filtered through a short silica gel bed. The filtrate was concentrated to a residue that was purified by flash chromatography to give the corresponding product Compound No. 877. Purity >99

$^1$H NMR: 5.43 (s, 1H), 7.60–7.75 (m, 4H), 7.80–7.85 (m, 2H), 7.92 (dd, J=8.0, 1.5 Hz, 1H), 8.14 (d, J=8.0 Hz, 1H), 8.30 (d, J=9.0 Hz, 1H), 9.08 (d, J=8.5 Hz, 1H). MS (MH$^+$): C$_{19}$H$_{11}$ClO$_2$S, Cal: 339; Found: 339.

Example 23

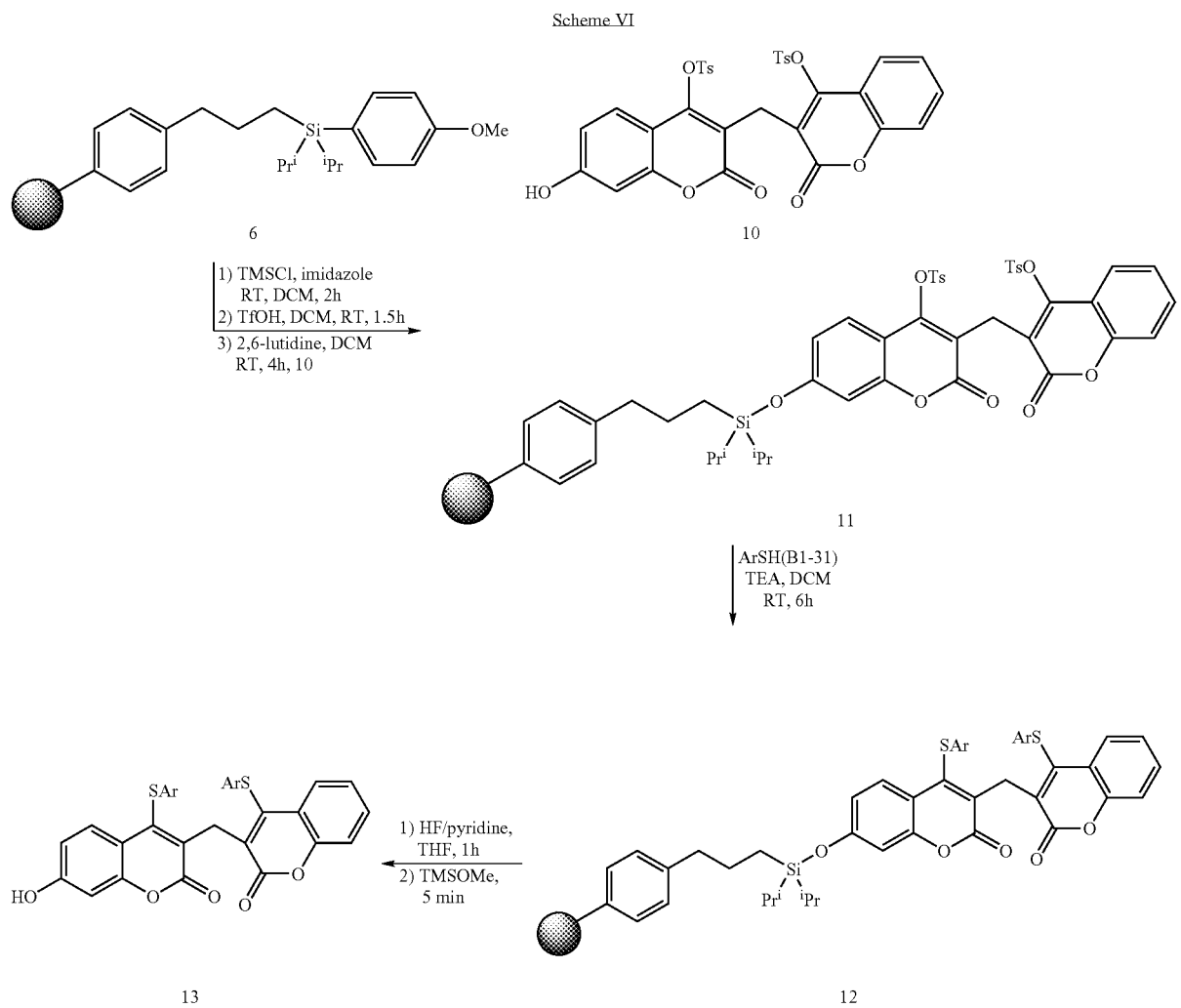

Scheme VI

Loading of Hydroxycoumarin 10 onto Resin 6

Silicon-functionalized resin 6 that had been dried under high vacuum for 12 hours was weighed (200 mg) into a 10 mL polypropylene PD-10 column fitted with a Teflon stopcock and swollen in a solution of trimethylsilyl chloride (0.1 mL) and imidazole (20 mg) in $CH_2Cl_2$ (4 mL) under $N_2$ atmosphere for 2 h. The solvent was then drained under positive $N_2$ pressure, and 0.2 mL of trifluoromethanesulfonic acid in $CH_2Cl_2$ (4 mL) was added by syringe. The resin turned red/orange upon acid treatment and was then gently agitated for 1.5 h while still under $N_2$ atmosphere. Once activation was completed, two $CH_2Cl_2$ washes removed excess acid. Then, 10 (2 equiv.) in 2,6-lutidine (0.8 mL) was added and the mixture resulted in a colorless resin. The beads are then gently agitated for an additional 4 hours under $N_2$ atmosphere. The beads were drained, exposed to atmosphere, and subjected to the following wash protocol: $CH_2Cl_2$ (5 mL, 2 h), DMF (5 mL, 2 h), MeOH (5 mL, 2 h), DMF (5 mL, 2 h), and $CH_2Cl_2$ (5 ML, 2 h). The resin 11 was air-dried for 3 h and then placed under high vacuum for 24 h to remove trace solvent and water.

Reaction of thiols with Resin 11

To a suspension of 11 (20 beads) with thiol (2.5 eq.) in dichloromethane (2 mL), triethylamine (3.0 eq.) was added at room temperature under air atmosphere. The beads are then gently agitated for an additional 6 hours under $N_2$ atmosphere. The beads were drained, exposed to atmosphere, and subjected to the following wash protocol: $CH_2Cl_2$ (2 mL, 2 h), DMF (2 mL, 2 h), MeOH (2 mL, 2 h), DMF (2 mL, 2 h), and $CH_2Cl_2$ (2 mL, 2 h). The resin 12 was then placed under high vacuum for 24 h to remove trace solvent and water.

Cleavage of 12 from Resin

Vacuum-dried resin 12 was transferred into a solvent-resistant scintillation vial and 200 μL of THF and 10 μL of HF/pyridine solution were added. The vial was sealed and agitated for 1 h, at which time 20 μL of methoxytrimethylsilane was added to quench unreacted HF. The beads are further agitated for 30 min to ensure complete quenching. The solution was removed and the beads washed twice. All solvents were combined and concentrated in vacuo to afford the final product 13.

Example 24

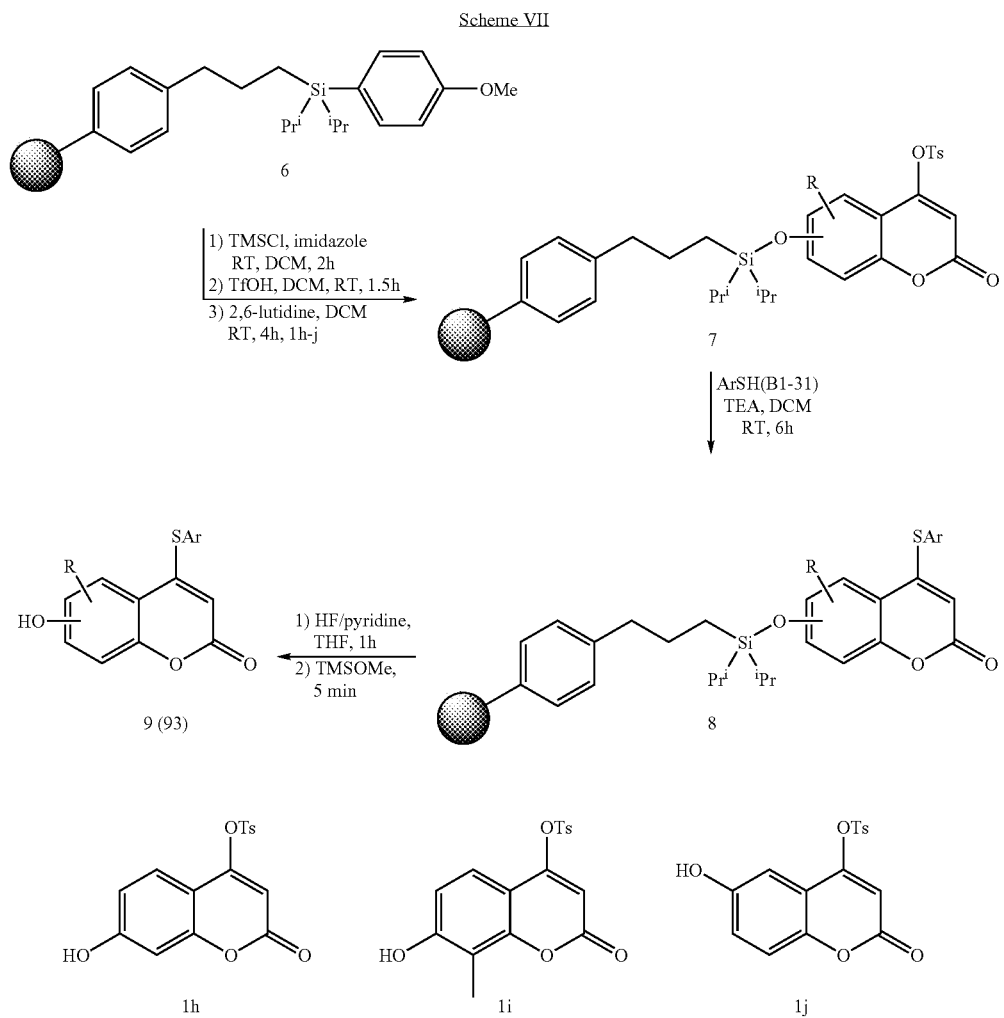

Loading of Hydroxycoumarin 1h-j onto Resin 6

Silicon-functionalized resin 6 that had been dried under high vacuum for 12 hours was weighed (200 mg) into a 10 mL polypropylene PD-10 column fitted with a Teflon stopcock and swollen in a solution of trimethylsilyl chloride (0.1 mL) and imidazole (20 mg) in CH$_2$Cl$_2$ (4 mL) under N$_2$ atmosphere for 2 h. The solvent was then drained under positive N$_2$ pressure, and 0.2 mL of trifluoromethanesulfonic acid in CH$_2$Cl$_2$ (4 mL) was added by syringe. The resin turned red/orange upon acid treatment and was then gently agitated for 1.5 hours while still under N$_2$ atmosphere. Once activation was completed, two CH$_2$Cl$_2$ washes removed excess acid. Then, 1h/1i/1j (2 equiv.) in 2,6-lutidine (0.8 mL) was added and the mixture resulted in a colorless resin. The beads are then gently agitated for an additional 4 hours under N$_2$ atmosphere. The beads were drained, exposed to atmosphere, and subjected to the following wash protocol: CH$_2$Cl$_2$ (5 mL, 2 h), DMF (5 mL, 2 h), MeOH (5 mL, 2 h), DMF (5 mL, 2 h), and CH$_2$Cl$_2$ (5 mL, 2 h). The resin 7 was air-dried for 3 h and then placed under high vacuum for 24 h to remove trace solvent and water.

Reaction of thiols with Resin 7

General Procedure from 7 to 8: To a suspension of 7 (20 beads) with thiol (1.5 eq.) in dichloromethane (2 mL), triethylamine (2.0 eq.) was added at room temperature under air atmosphere. The beads are then gently agitated for an additional 6 hours under N$_2$ atmosphere. The beads were drained, exposed to atmosphere, and subjected to the following wash protocol: CH$_2$Cl$_2$ (2 mL, 2 h), DMF (2 mL, 2 h), MeOH (2 mL, 2 h), DMF (2 mL, 2 h), and CH$_2$Cl$_2$ (2 mL, 2 h). The resin 8 was then placed under high vacuum for 24 h to remove trace solvent and water.

Cleavage of 8 from Resin

Vacuum-dried resin 8 was transferred into a solvent-resistant scintillation vial and 200 µL of THF and 10 µL of HF/pyridine solution were added. The vial was sealed and agitated for 1 h, at which time 20 µL of methoxytrimethylsilane was added to quench unreacted HF. The beads are further agitated for 30 min to ensure complete quenching. The solution was removed and the beads washed twice. All solvents were combined and concentrated in vacuo to afford the final product 9.

Example 25

General Procedure for 3-aryliodonio-2-oxo-2H-1-benzopyan-4-olates:

Scheme VIII

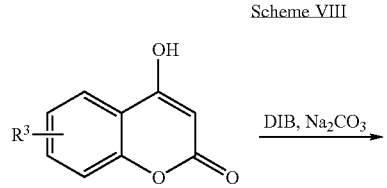

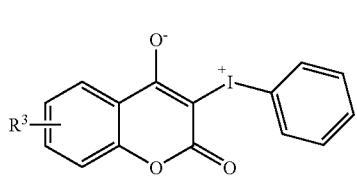

R³ = H 95%
R³ = 7-MeO 90%
R³ = 6-Me 94%
R³ = 6-F 90%
R³ = 6-Cl 80%
R³ = 6,8-diCl 52%

Iodobenzene diacetate (10 mmol) was suspended in a solution of $Na_2CO_3$ (10 mmol) in water (100 mL) and stirred for 30 min at rt. Then, a solution of 4-hydroxycoumarin (10 mmol) and $Na_2CO_3$ (10 mmol) in water (100 mL) was added. After stirring at rt for 2 hr, the precipitate was collected by filtration, washed several times with water, dried under vacuum. The resulting white solid was used without further purification.

Example 26

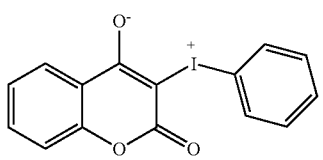

3-Phenyliodonio-2-oxo-2H-1-benzopyan-4-olate was prepared according to Scheme VIII. ¹H NMR δ 11.40 (br s, 1H), 8.00 (dd, J=7.5, 1.5 Hz, 1H), 7.66 (dt, J=7.5, 1.5 Hz, 1H), 7.44–7.32 (m, 7H); ¹³C NMR δ 162.6, 160.9, 153.0, 133.0, 132.7, 131.7, 128.7, 128.2, 124.7, 124.4, 117.1, 116.9, 106.8; LC-MS m/z 237 (M−1), 193.

Example 27

General Procedure for 2,3-dithiocoumarins

Scheme IX

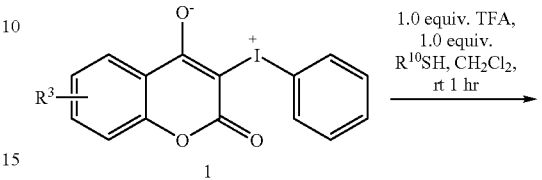

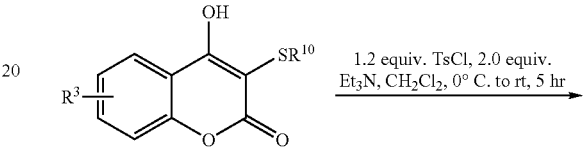

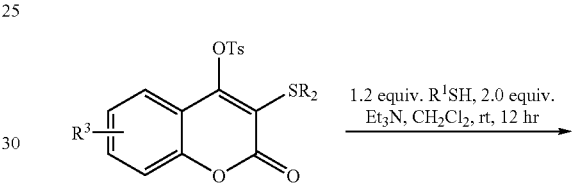

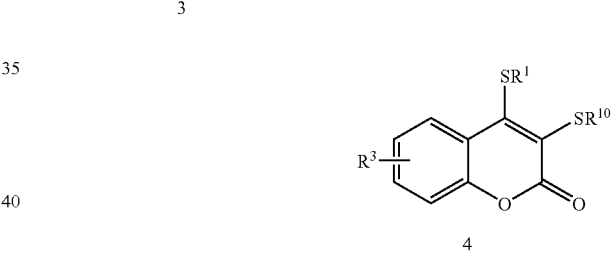

To a suspension of coumarin based iodonium ylide 1 (1 mmol) in $CH_2Cl_2$ (5 mL) was added thiol, $R^{10}SH$, (1.0 equiv.) at rt. The suspension turned to a clear solution immediately upon addition of TFA (1.0 equiv.). After 1 hr at rt, the solvent was removed under vacuum and purified on column. To a solution of 3-thio-4-hydroxycoumarin 2 (1 mmol) in $CH_2Cl_2$ (5 mL) was added $Et_3N$ (2.0 equiv.) at rt. TsCl (1.2 equiv.) was added to the above solution at 0° C. under argon. After 10 minutes, the ice-bath was removed and the reaction was stirred further for 5 hr. The reaction mixture was diluted with $CH_2Cl_2$ and washed with brine. The organic layer was separated, dried over $Na_2SO_4$, concentrated under vacuum, and purified on a column.

The purified 3-thio-4-tosylcoumarin 3 (1 mmol) was dissolved in $CH_2Cl_2$ (5 mL), followed by addition of $Et_3N$ (2.0 equiv.) and thiol, $R^1SH$, (1.2 equiv.) successively at rt. After being stirred for 12 hr, the solvent was removed under vacuum and the residue was purified with column chromatography.

Example 28

Scheme X

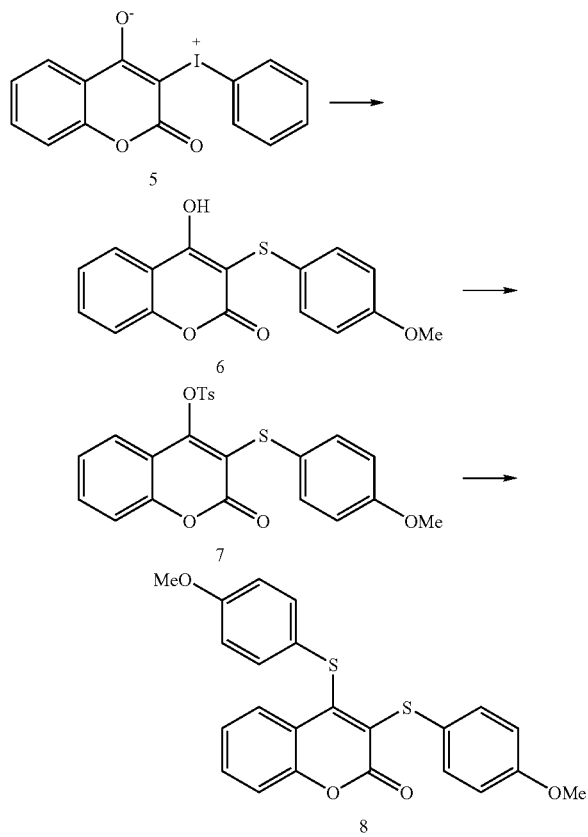

To a suspension of coumarin based iodonium ylide 5 (1 mmol) in CH$_2$Cl$_2$ (5 mL) was added 4-methoxybenzenethiol (1.0 equiv.) at rt. The suspension became a clear solution immediately upon addition of TFA (1.0 equiv.). After 1 hr at rt, the solvent was removed under vacuum and purified on a column.

To a solution of 6 (1 mmol) in CH$_2$Cl$_2$ (5 mL) was added Et$_3$N (2.0 equiv.) at rt. TsCl (1.2 equiv.) was added to the solution at 0° C. under argon. After 10 min, the ice-bath was removed and the reaction was stirred further for 5 hr. The reaction mixture was diluted with CH$_2$Cl$_2$ and washed with brine. The organic layer was separated, dried over Na$_2$SO$_4$, concentrated under vacuum, and purified on a column.

The purified 3-thio-4-tosylcoumarin 6 (1 mmol) was dissolved in CH$_2$Cl$_2$ (5 mL), followed by addition of Et$_3$N (2.0 equiv.) and 4-methoxybenzenethiol (1.2 equiv.) successively at rt. After being stirred for 12 hr, the solvent was removed under vacuum and the residue was purified with column chromatography.

6: $^1$H-NMR (500 MHz, d-DMSO) δ 7.93 (1H, d, J=8.0 Hz), 7.68 (1H, t, J=8.0 Hz), 7.39 (1H, d, J=8.0 Hz), 7.38 (1H, t, J=8.0 Hz), 7.24 (2H, d, J=9.0 Hz), 6.87 (2H, d, J=9.0 Hz), 3.68 (3H, s). $^{13}$C-NMR (125 MHz, d-DMSO) 168.08, 161.56, 158.92, 153.54, 134.20, 130.67, 126.57, 124.99, 124.94, 117.11, 116.32, 115.47, 97.30, 55.88. LC/MS 299 (M-1), 175, 131.

8: $^1$H-NMR (500 MHz, d-DMSO) δ 7.80 (1H, dd, J=8.5, 1.5 Hz), 7.55 (1H, dt, J=8.5, 1.5 Hz), 7.39 (1H, dd, J=8.0, 1.0 Hz), 7.34 (2H, d, J=8.5 Hz), 7.28 (2H, d, J=9.0 Hz,), 7.23 (1H, dt, J=8.5, 1.0 Hz), 6.90 (2H, d, J=9.0 Hz), 6.87 (2H, d, J=8.5 Hz), 3.74 (3H, s), 3.72 (3H, s). LC/MS 445 (M+Na), 423 (M+1), 316, 315, 283, 282, 256, 240.

Example 29

Normalized Viral Assay

Primary in vitro anti-HCV screen. The antiviral activity of test compounds were assayed in the stably HCV RNA-replicating cell line, AVA5, derived by transfection of the human hepatoblastoma cell line, Huh7 (Blight, et al., 2000, Science 290: 1972). The test compounds were added to dividing cultures once daily for three days. The media was changed with each addition of the compounds. Cultures generally start the assay at 30–50% confluence and reach confluence during the last day of treatment. Intracellular HCV RNA levels and cytotoxicity are assessed 24 hours after the last dose of compound.

Assays were conducted using a single dose of test compound. Duplicate cultures for HCV RNA levels (on 48-well plates) and triplicate cultures for cytotoxicity (on 96-well plates) are used. A total of 4 untreated control cultures, and duplicate cultures treated with 10 IU/ml α-interferon (the approximate EC$_{90}$ with no cytotoxicity), and 100 μM ribavirin (the approximate CC$_{90}$ with no antiviral activity) serve as positive antiviral and toxicity controls.

Intracellular HCV RNA levels were measured using a commercial assay (Veresant®, Bayer Diagnostics, Inc. Ross, et al. (2002) J. Virol. Meth. 101:159–168, Quantitation of hepatitic C virus RNA by third generation branched DNA-based signal amplification assay). Cytotoxicity was measured using an established neutral red dye uptake assay (Korba, B. E. and J. L. Gerin. 1992. Use of a standardized cell culture assay to determine activities of nucleoside analogs against hepatitis B virus relication. Antivir. Res. 19:55–70). HCV RNA levels in the treated cultures are expressed as a percentage of the mean levels of RNA detected in untreated cultures. A level of 30% or less, HCV RNA relative to control cultures may be considered to be a positive antiviral effect. A level of 50% or less, neutral red dye uptake relative to control cultures may be considered to be a cytotoxic effect.

Within normal variations, levels of intracellular HCV RNA remained constant among different untreated cultures. Both treatment controls responded as expected within normal parameters. The positive test control, α-interferon (purchased from PBL Biomedical Laboratories, piscataway, N.J.), induced significant depressions of HCV RNA replication at the concentrations used. The negative ("false positive") treatment control, ribavirin (purchased from Sigma, Inc., St. Louis Mo.) induced loss of HCV RNA, but the reduction in cell viability was nearly equivalent.

TABLE 4

| Compound | Conc. | HCV Copies/ml | % Control | Neutral Red O.D. | % Control |
|---|---|---|---|---|---|
| untreated Cells | | 1423017 | 106 | 2.249 | 101 |
| untreated cells | | 1167843 | 87 | 2.215 | 99 |
| untreated cells | | 1220055 | 90 | 2.218 | 99 |
| untreated Cells | | 1583672 | 117 | 2.252 | 101 |
| rHu α-IFN | 10 IU/ml | 85467 | 6 | 2.291 | 103 |
| | | 71460 | 5 | 2.217 | 99 |
| Ribavirin | 100 μM | 180813 | 13 | 0.394 | 18 |
| | | 115331 | 9 | 0.378 | 17 |

TABLE 4-continued

| Compound | Conc. | HCV Copies/ml | % Control | Neutral Red O.D. | % Control |
|---|---|---|---|---|---|
| VQ_412 | 10 μM | 726473 | 54 | 2.269 | 102 |
|  |  | 656755 | 49 | 2.247 | 101 |
| VQ_437 | 10 μM | 556515 | 41 | 2.261 | 101 |
|  |  | 507191 | 38 | 2.202 | 99 |
| VQ_468 | 10 μM | 306102 | 23 | 2.55 | 101 |
|  |  | 318777 | 24 | 2.262 | 101 |
| VQ_473 | 10 μM | 529743 | 39 | 2.281 | 102 |
|  |  | 523506 | 39 | 2.222 | 99 |
| VQ_824 | 10 μM | 1357786 | 101 | 2.214 | 99 |
|  |  | 1211659 | 90 | 2.274 | 102 |
| VQ_894 | 10 μM | 1277826 | 95 | 2.234 | 100 |
|  |  | 1128325 | 84 | 2.257 | 101 |
| VQ_899 | 10 μM | 886875 | 66 | 2.237 | 100 |
|  |  | 873484 | 65 | 2.286 | 102 |
| VQ_901 | 10 μM | 851852 | 63 | 2.287 | 102 |
|  |  | 846803 | 63 | 2.241 | 100 |
| VQ_902 | 10 μM | 124712 | 9 | 2.122 | 95 |
|  |  | 92446 | 7 | 2.228 | 100 |
| VQ_904 | 10 μM | 1072174 | 79 | 2.237 | 100 |
|  |  | 1013181 | 75 | 2.255 | 101 |
| VQ_910 | 10 μM | 266217 | 20 | 2.214 | 99 |
|  |  | 246717 | 18 | 2.293 | 103 |

TABLE 5

| | MTS Cell Viability | | | ATP Cell Viability | | | Normalized Viral Assay | | |
|---|---|---|---|---|---|---|---|---|---|
| Comp. | 10 μM | 5 μM | 1 μM | 10 μM | 5 μM | 1 μM | 10 μM | 5 μM | 1 μM |
| 412 | 95.34 | 112.38 | 114.98 | 62.95 | 101.74 | 97.96 | 16.13 | 28.13 | 55.65 |
| 437 | 105.87 | 110.95 | 114.85 | 74.11 | 100.32 | 107.54 | 20.41 | 34.83 | 59.33 |
| 468 | 96.64 | 103.01 | 108.87 | 48.49 | 92.70 | 98.82 | 18.06 | 35.09 | 72.14 |
| 473 | 80.12 | 102.88 | 109.11 | 56.69 | 100.92 | 107.74 | 12.45 | 40.79 | 68.16 |
| 830 | 98.85 | 101.06 | 112.38 | 104.41 | 97.11 | 106.44 | 40.35 | 46.87 | 87.63 |
| 824 | 84.15 | 94.56 | NA | 75.61 | 91.28 | NA | 17.28 | 52.29 | NA |
| 899 | 85.37 | 90.22 | 106.10 | 105.60 | 112.43 | 102.77 | 10.32 | 10.66 | 40.10 |
| 904 | 86.22 | 108.04 | 116.41 | 74.11 | 100.32 | 107.54 | 9.27 | 37.87 | 50.52 |
| 901 | 86.10 | 97.37 | 107.32 | 79.01 | 106.63 | 105.62 | 8.34 | 12.80 | 24.87 |
| 894 | 81.24 | 83.91 | 104.53 | 58.26 | 109.42 | 113.25 | 6.84 | 9.04 | 35.65 |
| 902 | 84.52 | 86.70 | 116.05 | 62.95 | 101.74 | 97.96 | 5.61 | 12.03 | 41.92 |
| 910 | 79.43 | 92.64 | 105.74 | 84.78 | 97.48 | 115.34 | 3.41 | 9.51 | 32.93 |

Example 26

Secondary in vitro Anti-HCV Dose-Response Assay.

Dividing cultures of AVA5 cells are treated once daily for three days (media is changed with each addition of compound) with 4 concentrations of test compound (2 cultures per concentration). A total of 4 untreated control cultures, and duplicate cultures treated with 10, 3.0, and 1.0 IU/ml α-interferon (active antiviral with no cytotoxicity), and 100 μM ribavirin (no antiviral activity and cytotoxic) serve as controls. Intracellular HCV RNA levels and cytotoxicity are assessed 24 hours following the last treatment as described for the primary assays. The 50% and 90% effective antiviral concentrations ($EC_{50}$, $EC_{90}$) and the 50% cytotoxic concentrations ($CC_{50}$) are calculated and used to generate Selectivity Indexes (S.I., $CC_{50}/EC_{50}$). An S.I of 10, or greater, may be considered to be a selective antiviral effect. The selectivity indexes (S.I.) of test compounds against HCV repliclicons in AVA5 cell cultures is presented in Table 6

TABLE 6

| Compound | $CC_{50}$ (μM) | $EC_{50}$ (μM) | $EC_{90}$ (μM) | S.I. ($CC_{50}/EC_{90}$) |
|---|---|---|---|---|
| α-interferon | >10000[1,2] | 1.8 ± 0.2[1] | 8.2 ± 0.6[1] | >5556 |
| ribavirin | 54 ± 2.4 | 29 ± 2.5 | 140 ± 11 | 1.9 |
| 468 | >300[2] | 1.2 ± 0.1 | 8.3 ± 0.6 | >250 |
| 902 | >300[2] | 0.491 ± 0.024 | 5.2 ± 0.6 | >611 |
| 910 | >300[2] | 1.4 ± 0.1 | 12 ± 1.1 | >214 |

[1]Values for α-interferon are expressed in IU/ml.
[2]No significant cytotoxic effects were observed up to the highest indicated concentration.

The values presented in Table 6 were calculated by linear regression analysis using data from all treated cultures. The standard deviation was calculated using the error of regression generated from the linear regression analysis.

Analysis of intracellular HCV RNA was performed 24 hours following the final treatment. A total of three cultures were treated a each concentration for each compound. HCV RNA levels were normalized to the level of β-actin RNA in each individual sample. The intracellular HCV RNA levels at various concentrations of the test compound are provided in Table 7.

TABLE 7

| | Intracellular HCV RNA Levels (genomic copies/cell) | | | |
|---|---|---|---|---|
| Compound | 10 IU/ml | 3.0 IU/ml | 1.0 IU/ml | |
| α-interferon | 103060 ± 14470 | 329605 ± 26035 | 1169765 ± 37135 | |
| | 300 mM | 100 mM | 30 mM | 10 mM |
| ribavirin | — | 250445 ± 5015 | 640505 ± 29715 | 1379495 ± 69125 |

TABLE 7-continued

| Intracellular HCV RNA Levels (genomic copies/cell) | | | | |
|---|---|---|---|---|
| 468 | 56535 ± 8005 | 194410 ± 7620 | 473805 ± 21625 | 1317765 ± 55645 |
| 902 | 12940 ± 5640 | 91645 ± 7385 | 332975 ± 6745 | 919880 ± 44000 |
| 910 | 58165 ± 7635 | 163575 ± 6325 | 494605 ± 6235 | 1176970 ± 27620 |

The level of HCV RNA in the 6 control (untreated) cultures in these experiments was 1391755±11225 copies/ml.

Those with skill in the art may recognize various modifications to the embodiments of the invention described and illustrated herein. Such modifications are intended to be covered by the spirit and scope of the present invention. That is, while the invention has been described in detail with reference to certain embodiments, it will be recognized by those skilled in the art that there are other embodiments of the invention within the spirit and scope of the claims.

What is claimed is:

1. A compound of the formula XI:

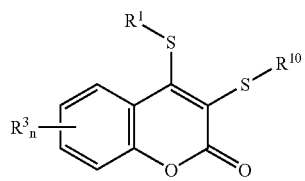

wherein
$R^1$ and $R^{10}$ are independently selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;
$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

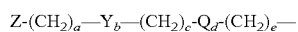

wherein Y and Q are independently selected from an aromatic group, O, S, —CR=CR—,

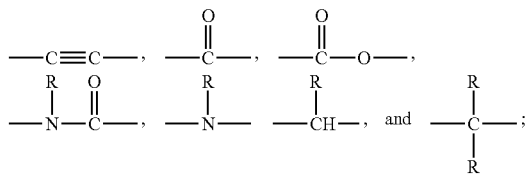

each R is independently selected from H or lower alkyl, Z is selected from H, —CO$_2$R, —OR, —SR, —NR$_2$,

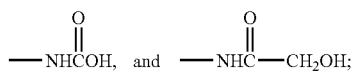

a, C and e are independently selected from values from 0 to 10;
b and d are independently selected from 0 and 1, provided that when a=0 then b=0, and when c=0 then d=0;
or $R^3$ may occupy two adjacent positions to form a fused aromatic ring; and
n is selected from values between 0 and 4.

2. The compound of claim 1, having the formula XII

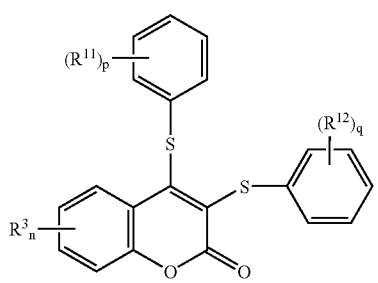

wherein
each $R^{11}$ is independently selected from halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
each $R^{12}$ is independently selected from halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
$R_3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or R3 is a group of the formula

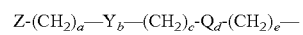

wherein Y and Q are independently selected from an aromatic group, O, S, —CR=CR—,

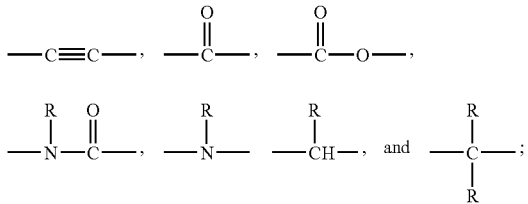

each R is independently selected from H or lower alkyl,
Z is selected from H, —CO$_2$R, —OR, —SR, —NR$_2$,

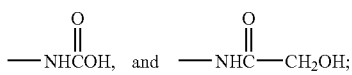

a, c and e are independently selected from values from 0 to 10;

b and d are independently selected from 0 and 1, provided that when a=0 then b=0, and when c=0 then d=0;

or R$^3$ may occupy two adjacent positions to form a fused aromatic ring;

n is selected from values between 0 and 4;
p is selected from values between 0 and 5; and
q is selected from values between 0 and 5.

3. The compound of claim 2, having the formula XII$_a$:

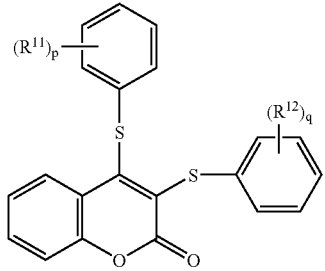

(XII$_a$)

wherein
each R$^{11}$ is independently selected from halogen, hydroxy, lower alkyl, lower alkenyl, lower alkynyl, lower alkoxy, thio-lower alkyl, C$_1$–C$_8$ acyl, lower alkyl ester, amide, and lower alkyl amide;

each R$^{12}$ is independently selected from halogen, hydroxy, lower alkyl, lower alkenyl, lower alkynyl, lower alkoxy, thio-lower alkyl, C$_1$–C$_8$ acyl, lower alkyl ester, amide, and lower alkyl amide;

p is selected from values between 0 and 5; and
q is selected from values between 0 and 5.

4. The compound of claim 3, having the formula

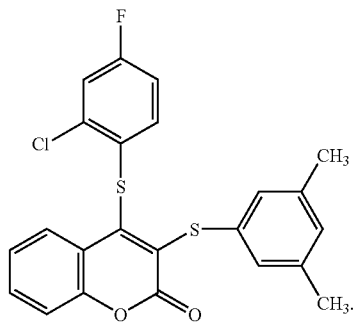

5. The compound of claim 3, having the formula

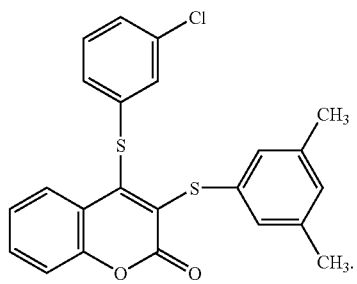

6. The compound of claim 3, having the formula

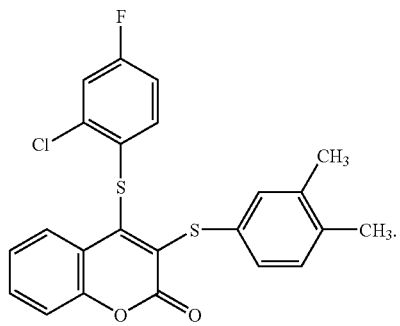

7. The compound of claim 3, having the formula

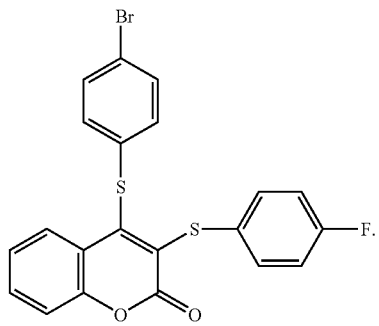

8. A method of treating HCV infection comprising administering a therapeutically effective amount of a compound of Formula I

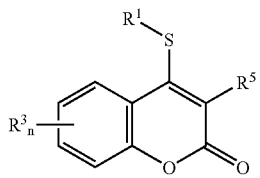

(I)

wherein
  $R^1$ is selected from
    an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
    a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
    an unsubstituted or substituted alkyl group, wherein the substituted alkyl group may be substituted with one or more halogen, hydroxy, and lower alkoxy; and
    an unsubstituted or substituted cycloalkyl group, wherein the substituted cycloalkyl group may be substituted with one or more halogen, hydroxy, and lower alkoxy;
  $R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula

wherein Y and Q are independently selected from an aromatic group, O, S, —CR═CR—,

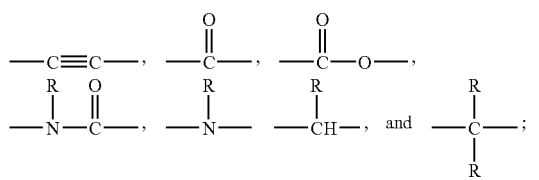

each R is independently selected from H or lower alkyl, Z is selected from H, —CO$_2$R, —OR, —SR, —NR$_2$,

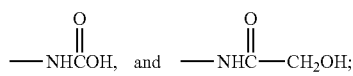

a, c and e are independently selected from values from 0 to 10;

b and d are independently selected from 0 and 1, provided that when a=0 then b=0, and when c=0 then d=0;
or $R^3$ may occupy two adjacent positions to form a fused aromatic ring,
n is selected from values between 0 and 4;
$R^5$ is selected from hydrogen, lower alkyl, lower alkenyl, lower alkynyl, lower aralkyl, aryl, thioalkyl, thioaryl, and thioaralkyl,
each of which may be unsubstituted or substituted with one or more substituents selected from halogen, lower alkyl, and lower alkoxy, thio-lower alkyl, $C_1$–$C_8$ acyl, lower alkyl ester, amide, and lower alkyl amide; or $R^5$ may be a group of the formula

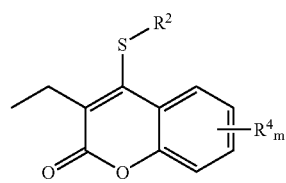

wherein
  $R^2$ is selected from
    an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
    a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
    an unsubstituted or substituted alkyl group, wherein the substituted alkyl group may be substituted with one or more halogen, hydroxy, and lower alkoxy; and
    an unsubstituted or substituted cycloalkyl group, wherein the substituted cycloalkyl group may be substituted with one or more halogen, hydroxy, and lower alkoxy;
  $R^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^4$ is a group of the formula

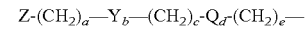

wherein Y and Q are independently selected from an aromatic group, O, S, —CR═CR—,

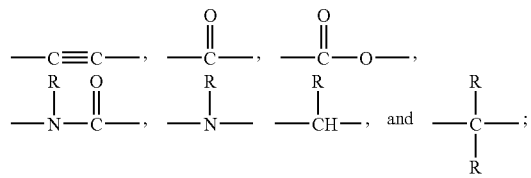

each R is independently selected from H or lower alkyl, Z is selected from H, —CO$_2$R, —OR, —SR, —NR$_2$,

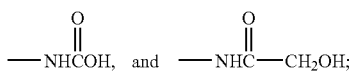

a, c and e are independently selected from values from 0 to 10;

b and d are independently selected from 0 and 1, provided that when a=0 then b=0, and when c=0 then d=0;

or $R^4$ may occupy two adjacent positions to form a fused aromatic ring, and, m is selected from values between 0 and 4, in a pharmaceutically acceptable carrier.

9. The method of claim 8, comprising administering a compound of the formula II,

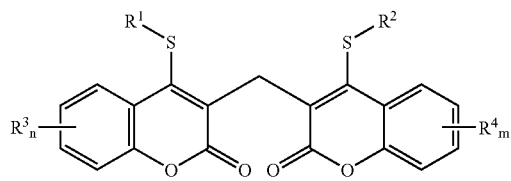

(II)

wherein
R$^1$ and R$^2$ are independently selected from
  an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
  an unsubstituted or substituted alkyl group, wherein the substituted alkyl group may be substituted with one or more halogen, hydroxy, and lower alkoxy; and
  an unsubstituted or substituted cycloalkyl group, wherein the substituted cycloalkyl group may be substituted with one or more halogen, hydroxy, and lower alkoxy; and each $R^3$ and $R^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula Z-(CH$_2$)$_a$—Y$_b$—(CH$_2$)$_c$-Q$_d$-(CH$_2$)$_e$— wherein Y and Q are independently selected from an aromatic group, O, S, —CR=CR—,

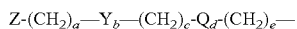

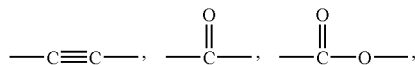

each R is independently selected from H or lower alkyl, Z is selected from H, —CO$_2$R, —OR, —SR, —NR$_2$,

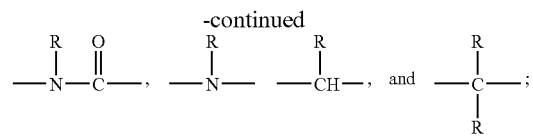

a, c and e are independently selected from values from 0 to 10;

b and d are independently selected from 0 and 1, provided that when a=0 then b=0, and when c=0 then d=0;

or $R^3$ or $R^4$ may occupy two adjacent positions to form a fused aromatic ring, and n and m are independently selected from values between 0 and 4.

10. The method of claim 8, comprising administering a compound of the Formula III

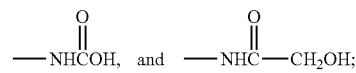

(III)

wherein $R^1$, $R^3$ and n are as described for the compound of Formula I.

11. The method of claim 10, wherein $R^1$ is selected from an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide.

12. The method of claim 11, wherein the unsubstituted or substituted aromatic group is an unsubstituted or substituted phenyl group.

13. The method of claim 12, comprising administering a compound having the formula

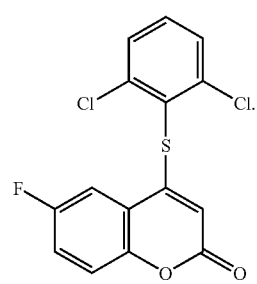

14. The method of claim 12, comprising administering a compound having the formula

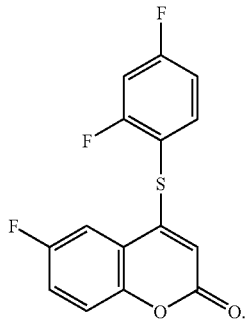

15. A method of treating HCV infection comprising administering a therapeutically effective amount of a compound according to claim 1.

16. A method of treating HCV infection comprising administering a therapeutically effective amount of a compound according to claim 2.

17. The method of claim 16, comprising administering a compound having the formula

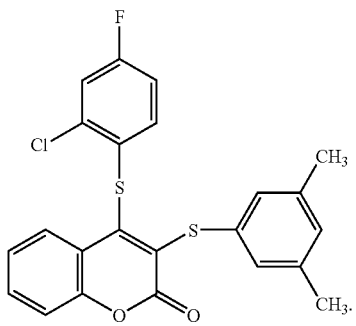

18. The method of claim 16, comprising administering a compound having the formula

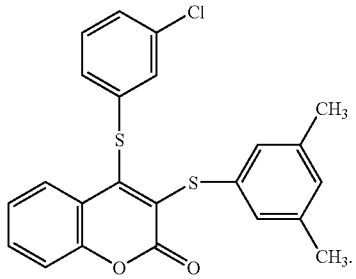

19. The method of claim 16, comprising administering a compound having the formula

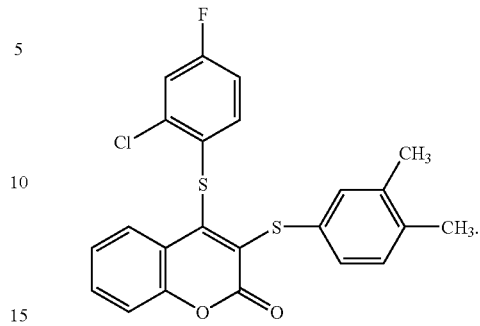

20. A pharmaceutical composition for the treatment of HCV infection comprising a therapeutically effective amount of a compound of Formula I

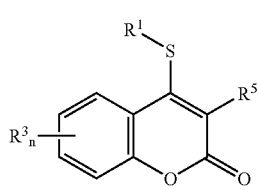

(I)

wherein
$R^1$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;

$R^3$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or $R^3$ is a group of the formula $$Z\text{-}(CH_2)_a\text{—}Y_b\text{—}(CH_2)_c\text{-}Q_d\text{-}(CH_2)_e\text{—}$$

wherein Y and Q are independently selected from an aromatic group, O, S, —CR═CR—,

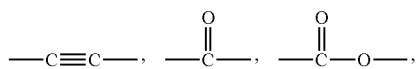

-continued

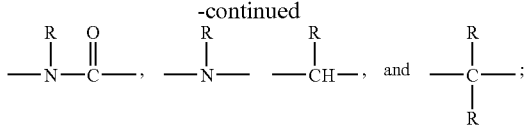

each R is independently selected from H or lower alkyl,
Z is selected from H, —CO$_2$R, —OR, —SR, —NR$_2$,

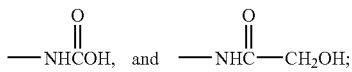

a, c and e are independently selected from values from 0 to 10;
b and d are independently selected from 0 and 1, provided that when a=0 then b=0, and when c=0 then d=0;
or R$^3$ may occupy two adjacent positions to form a fused aromatic ring,
n is selected from values between 0 and 4;
R$^5$ is selected from hydrogen, lower alkyl, lower alkenyl, lower alkynyl, lower aralkyl, aryl, thioalkyl, thioaryl, and thioaralkyl,
each of which may be unsubstituted or substituted with one or more substituents selected from halogen, lower alkyl, and lower alkoxy, thio-lower alkyl, C$_1$–C$_8$ acyl, lower alkyl ester, amide, and lower alkyl amide; or R$^5$ may be a group of the formula

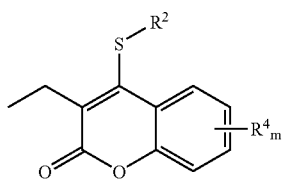

wherein
R$^2$ is selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, C$_1$–C$_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, C$_1$–C$_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy;
R$^4$ is selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or R$^4$ is a group of the formula Z-(CH$_2$)$_a$—Y$_b$—(CH$_2$)$_c$-Q$_d$-(CH$_2$)$_e$— wherein Y and Q are independently selected from an aromatic group, O, S, —CR=CR—,

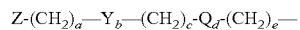

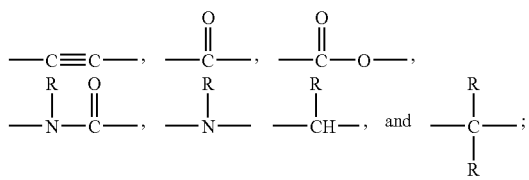

each R is independently selected from H or lower alkyl,
Z is selected from H, —CO$_2$R, —OR, —SR, —NR$_2$,

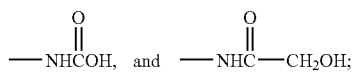

a, c and e are independently selected from values from 0 to 10;
b and d are independently selected from 0 and 1, provided that when a=0 then b=0, and when c=0 then d=0;
or R$^4$ may occupy two adjacent positions to form a fused aromatic ring,
and, m is selected from values between 0 and 4,
in a pharmaceutically acceptable carrier.
21. The pharmaceutical composition of claim 20, comprising a compound of the formula II, (II)

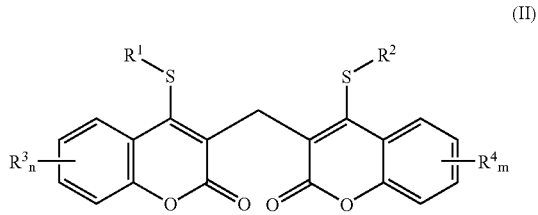

wherein
R$^1$ and R$^2$ are independently selected from
an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, C$_1$–C$_8$ acyl, lower alkyl ester, amide, and lower alkyl amide;
a substituted or unsubstituted aralkyl group, wherein the substituted aralkyl group may be substituted with one or more of halogen, hydroxy, lower alkyl, lower alkenyl, lower alkynyl, lower alkoxy, thio-lower alkyl, C$_1$–C$_8$ acyl, lower alkyl ester, amide, and lower alkyl amide;
an unsubstituted or substituted alkyl group, wherein the substituted alkyl group may be substituted with one or more halogen, hydroxy, and lower alkoxy; and
an unsubstituted or substituted cycloalkyl group, wherein the substituted cycloalkyl group may be substituted with one or more halogen, hydroxy, and lower alkoxy; and each $R^3$ and $R^4$ is independently selected from halogen, hydroxy, amino, lower alkyl, lower alkoxy, lower alkenyl, and lower alkynyl, wherein the lower alkyl, lower alkoxy, lower alkenyl and lower alkynyl may be unsubstituted or may be substituted with one or more of halogen, hydroxy, and lower alkoxy; or is a group of the formula

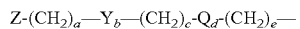

wherein Y and Q are independently selected from an aromatic group, O, S, —CR=CR—,

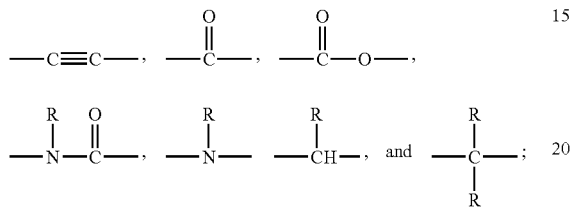

each R is independently selected from H or lower alkyl, Z is selected from H, —CO$_2$R, —OR, —SR, —NR$_2$,

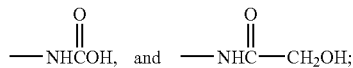

a, c and e are independently selected from values from 0 to 10;

b and d are independently selected from 0 and 1, provided that when a=0 then b=0, and when c=0 then d=0;

or or may occupy two adjacent positions to form a fused aromatic ring, and n and m are independently selected from values between 0 and 4.

22. The pharmaceutical composition of claim 20, comprising a compound of the Formula III

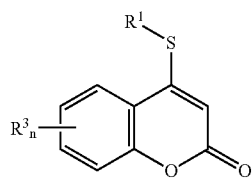

wherein $R^1$, $R^3$ and n are as described for the compound of Formula I.

23. The pharmaceutical composition of claim 22, wherein $R^1$ is selected from an unsubstituted or substituted aromatic group, wherein the substituted aromatic group may be substituted with one or more of halogen, hydroxy, lower alkyl, lower alkenyl, lower alkynyl, lower alkoxy, thio-lower alkyl, $C_1$–$C_8$ acyl, lower alkyl ester, amide, and lower alkyl amide.

24. The pharmaceutical composition of claim 23, wherein the unsubstituted or substituted aromatic group is an unsubstituted or substituted phenyl group.

25. The pharmaceutical composition of claim 23, comprising a compound having the formula

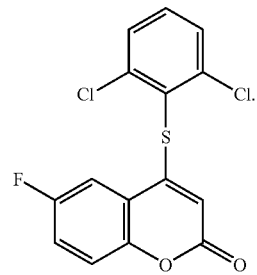

26. The pharmaceutical composition of claim 23, comprising a compound having the formula

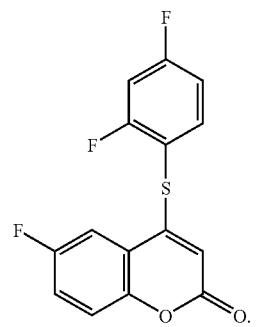

27. A pharmaceutical composition for the treatment of HCV infection comprising a therapeutically effective amount of a compound according to claim 1 in a pharmaceutically acceptable carrier.

28. A pharmaceutical composition for the treatment of HCV infection comprising a therapeutically effective amount of a compound according to claim 2 in a pharmaceutically acceptable carrier.

29. The pharmaceutical composition of claim 28, comprising a compound having the formula

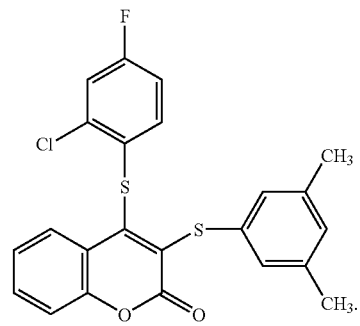

30. The pharmaceutical composition of claim 28, comprising a compound having the formula
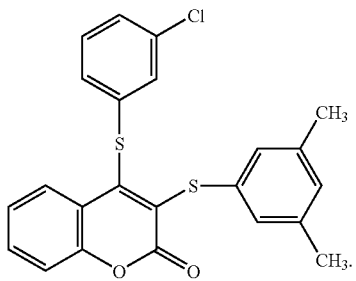
31. The pharmaceutical composition of claim 28, comprising a compound having the formula
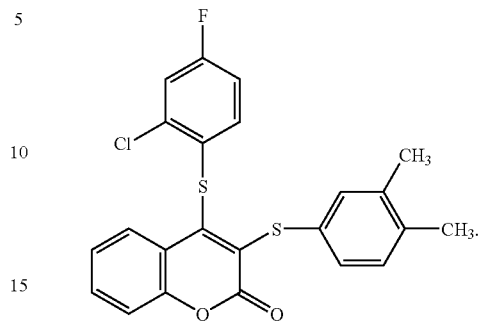
* * * * *